(12) United States Patent
Zingman et al.

(10) Patent No.: US 11,634,466 B2
(45) Date of Patent: Apr. 25, 2023

(54) MUSCLIN PEPTIDES AND METHODS OF USE THEREOF

(71) Applicant: UNIVERSITY OF IOWA RESEARCH FOUNDATION, Iowa City, IA (US)

(72) Inventors: Leonid Zingman, Iowa City, IA (US); Denice Hodgson-Zingman, Iowa City, IA (US)

(73) Assignee: University Of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 16/414,263

(22) Filed: May 16, 2019

(65) Prior Publication Data

US 2019/0270785 A1 Sep. 5, 2019

Related U.S. Application Data

(62) Division of application No. 15/841,648, filed on Dec. 14, 2017, now abandoned.

(60) Provisional application No. 62/434,256, filed on Dec. 14, 2016.

(51) Int. Cl.
| | |
|---|---|
| C07K 14/52 | (2006.01) |
| A61P 21/00 | (2006.01) |
| A61K 38/27 | (2006.01) |
| A61K 38/22 | (2006.01) |
| A61K 38/19 | (2006.01) |
| A61K 9/00 | (2006.01) |

(52) U.S. Cl.
CPC .............. *C07K 14/52* (2013.01); *A61K 38/19* (2013.01); *A61K 38/2242* (2013.01); *A61K 38/27* (2013.01); *A61P 21/00* (2018.01); *A61K 9/0019* (2013.01)

(58) Field of Classification Search
CPC .......... C07K 14/52; A61P 21/00; A61K 38/27
See application file for complete search history.

(56) References Cited

U.S. PATENT DOCUMENTS

| | | | |
|---|---|---|---|
| 4,612,302 A | 9/1986 | Szabo et al. | |
| 4,684,620 A | 8/1987 | Hruby et al. | |
| 4,853,371 A | 8/1989 | Coy et al. | |
| 4,938,949 A | 7/1990 | Borch et al. | |
| 7,425,531 B2 | 9/2008 | Lanctot et al. | |
| 7,470,668 B2* | 12/2008 | Lanctot | A01K 67/0275 435/69.5 |
| 2003/0125258 A1* | 7/2003 | Lanctot | C07K 14/51 435/325 |
| 2005/0143562 A1 | 6/2005 | Lanctot et al. | |
| 2007/0049521 A1 | 3/2007 | Lanctot et al. | |
| 2011/0104705 A1* | 5/2011 | Kita | A61P 9/10 435/7.1 |
| 2012/0316114 A1 | 12/2012 | Wendt et al. | |
| 2015/0359849 A1* | 12/2015 | Greenberg | A61K 38/1709 514/17.8 |
| 2018/0194824 A1 | 7/2018 | Zingman et al. | |

FOREIGN PATENT DOCUMENTS

| | | |
|---|---|---|
| EP | 2030021 B1 | 11/2012 |
| WO | 2008027855 A2 | 3/2008 |
| WO | 2014121083 A1 | 8/2014 |

OTHER PUBLICATIONS

Moffatt et al., 2009, Osteocrin—Beyond just another bone protein?, Cell Mol Life Sci, 66: 1135-1139.*
Lin et al., 2014, Characterization of Musclin as a New Target for Treatment of Hypertension, BioMed Research International, 7 pages.*
Li et al., 2013, Role of Musclin in the pathogenesis of Hypertension in Rat, PLOS One, 8(8): e72004 (9 pages).*
Pollen et al., Nov. 23, 2016, Primate Neurons Flex Their Musclin, Neuron, 92: 681-683.*
Moffatt et al., 2007, Osteocrin Is a Specific Ligand of the Natriuretic peptide Clearance Receptor That Modulates Bone Growth, The Journal of Biological Chemistry, 282(50): 36454-36462.*
Thomas et al., 2003, Osteocrin, a Novel Bone-specific Secreted Protein That Modulates the Osteoblast Phenotype, The Journal of Biological Chemistry, 278(50): 50563-50571.*
Finsterer, J , "Biomarkers of peripheral muscle fatigue during exercise", BMC Musculoskeletal Disorders 13, 218, 13 pages (2012).
Koulmann, N , et al., "Interaction between signalling pathways involved in skeletal muscle responses to endurance exercise", Pflugers Arch—Eur J Physiol 452, 125-139 (2006).
Liu, Y , et al., "Musclin inhibits insulin activation of Akt/protein kinase B in rat skeletal muscle", Journal of Internal Medicine Research 36, 496-504 (2008).
Nishizawa, H , et al., "Musclin, a novel skeletal muscle-derived secretory factor", Journal of Biological Chemistry 279(19), 19391-19395 (2004).
Parra, V , et al., "Insulin Stimulates Mitochondrial Fusion and Function in Cardiomyocytes via the Akt-mTOR-NFκB-Opa-1 Signaling Pathway", Diabetes 63(1), 75-88 (2014).
Sierra, A , et al., "Disruption of ATP-sensitive potassium channel function in skeletal muscles promotes production and secretion of musclin", Biochem Biophys Res Commun 471(1), 129-134 (2016).
Subbotina, E , et al., "Musclin is an activity-stimulated myokine that enhances physical endurance", PNAS 112(52), 16042-16047 (2015).

(Continued)

*Primary Examiner* — Amber D Steele
(74) *Attorney, Agent, or Firm* — Viksnins Harris Padys Malen LLP

(57) ABSTRACT

In certain embodiments, the present invention provides a musclin peptide and methods of increasing muscle growth, performance, resistance to injury and/or preventing or reducing muscle atrophy and improving overall skeletal muscle, metabolic and cardiac health in an animal in need thereof by administering a musclin peptide.

18 Claims, 20 Drawing Sheets

Specification includes a Sequence Listing.

(56) References Cited

OTHER PUBLICATIONS

Wang, W., et al., "Cloning and expression of the pig skeletal muscle musclin gene", Sheng WuGong Cheng Xue Bao 24(7), 1248-1252 (2008) [English Abstract].

\* cited by examiner

SEQUENCE LISTING

```
<160> NUMBER OF SEQ ID NOS: 28

<210> SEQ ID NO 1
<211> LENGTH: 51
<212> TYPE: PRT
<213> ORGANISM: Homo sapiens

<400> SEQUENCE: 1

Ser Phe Ser Gly Phe Gly Ser Pro Leu Asp Arg Leu Ser Ala Gly Ser
1               5                   10                  15

Val Asp His Lys Gly Lys Gln Arg Lys Val Val Asp His Pro Lys Arg
            20                  25                  30

Arg Phe Gly Ile Pro Met Asp Arg Ile Gly Arg Asn Arg Leu Ser Asn
        35                  40                  45

Ser Arg Gly
    50

<210> SEQ ID NO 2
<211> LENGTH: 33
<212> TYPE: PRT
<213> ORGANISM: Homo sapiens

<400> SEQUENCE: 2

Ser Phe Ser Gly Phe Gly Ser Pro Leu Asp Arg Leu Ser Ala Gly Ser
1               5                   10                  15

Val Asp His Lys Gly Lys Gln Arg Lys Val Val Asp His Pro Lys Arg
            20                  25                  30

Arg
```

```
<210> SEQ ID NO 3
<211> LENGTH: 51
<212> TYPE: PRT
<213> ORGANISM: Mus sp.

<400> SEQUENCE: 3

Ser Phe Ser Gly Phe Gly Ser Pro Leu Asp Arg Leu Ser Ala Gly Ser
1               5                   10                  15

Val Glu His Arg Gly Lys Gln Arg Lys Ala Val Asp His Ser Lys Lys
            20                  25                  30

Arg Phe Gly Ile Pro Met Asp Arg Ile Gly Arg Asn Arg Leu Ser Ser
        35                  40                  45

Ser Arg Gly
    50

<210> SEQ ID NO 4
<211> LENGTH: 33
<212> TYPE: PRT
<213> ORGANISM: Mus sp.

<400> SEQUENCE: 4

Ser Phe Ser Gly Phe Gly Ser Pro Leu Asp Arg Leu Ser Ala Gly Ser
1               5                   10                  15

Val Glu His Arg Gly Lys Gln Arg Lys Ala Val Asp His Ser Lys Lys
            20                  25                  30

Arg

<210> SEQ ID NO 5
<211> LENGTH: 4
<212> TYPE: PRT
<213> ORGANISM: Unknown
<220> FEATURE:
<223> OTHER INFORMATION: Description of Unknown: Musclin putative serine
      protease cleavage site peptide

<400> SEQUENCE: 5

Lys Lys Lys Arg
1

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atgttacaga acatttgatc cattacgaca                                              30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcacttcac attaaaaatt cttcactgc                                               29

<210> SEQ ID NO 8
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tagtatgcca tggtatttgt gctgtggg                                              28

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgctggttac tttctcttca agggcag                                               27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgatttgta cctaccttgg tgcctgc                                               27

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acccatcaca tacacactgc ctttacctac                                            30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gaacttcctg actagggag gagtagaagg                                             30

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctcttctctg gctgtgggtg gagac                                                 25

<210> SEQ ID NO 14
<211> LENGTH: 32
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 14
gtgaggttat gaacattcca acagctatat cc                                    32

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atggggttat tttccttgtc cacctacc                                         28

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggacctctcg aagtgttgga tac                                              23

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gctcatctta ggctttgtat ttggct                                           26

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgtggactta gcatcacagg                                                  20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agctgagagt ctgtcaagg                                                   19

<210> SEQ ID NO 20
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 20
tgatgtgaat gacttggata cagaca                                          26

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gctcattgtt gtactggttg gatatg                                          26

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggaatgtgga gcgtgctaaa a                                               21

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgctggaaaa acacttcgga ata                                             23

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgcagcacct ttggagaa                                                   18

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cccgacctgt ggaatacttg                                                 20

<210> SEQ ID NO 26
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 26
cagctcaagg gcacagtgc                                                    19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtggcccaag tcttgctcc                                                    19

<210> SEQ ID NO 28
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Phe Ser Gly Phe Gly Ser Pro Leu Asp Arg Leu Ser Ala Gly Ser
1               5                   10                  15

Val Glu His Arg Gly Lys Gln Arg Lys Ala Val Asp His Ser Lys Lys
            20                  25                  30

Arg
```

MUSCLIN PEPTIDES AND METHODS OF USE THEREOF

CLAIM OF PRIORITY

This application is a divisional application of U.S. patent application Ser. No. 15/841,648 that was filed on Dec. 14, 2017, which claims priority to U.S. Provisional Application No. 62/434,256 that was filed on Dec. 14, 2016. The entire content of these applications referenced above are hereby incorporated by reference herein.

STATEMENT REGARDING FEDERALLY SPONSORED RESEARCH

This invention was made with government support under HL113089, HL093368 and DK092412 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 22, 2018, is named 17023_208US1_SL.txt and is 7,603 bytes in size.

BACKGROUND

Skeletal muscles are critical for physical activity and metabolic homeostasis while muscle loss is the common outcome of aging, inactivity, inadequate nutrition and numerous pathological conditions resulting in increased morbidity and mortality. Accordingly, new treatments are needed to minimize the loss of muscle mass.

SUMMARY

In certain embodiments, the present invention provides a musclin peptide comprising an amino acid sequence having at least 80% identity to SEQ ID NO: 1 or SEQ ID NO:2 (human) or SEQ ID NO: 3 or SEQ ID NO:4 (mouse). In certain embodiments, the musclin peptide comprises an amino acid sequence having 100% identity to SEQ ID NO:1 or SEQ ID NO:2.

In certain embodiments, the present invention provides a therapeutic composition comprising the musclin peptide comprising an amino acid sequence having at least 80% identity to SEQ ID NO: 1 or SEQ ID NO:2 (human) or SEQ ID NO: 3 or SEQ ID NO:4 (mouse), and a pharmaceutically acceptable carrier.

In certain embodiments, the present invention provides a method of increasing muscle growth, performance, resistance to injury and/or preventing or reducing muscle atrophy in an animal in need thereof, comprising administering a musclin peptide having at least 80% identity to SEQ ID NO:1, SEQ ID NO:2, SEQ ID NO:3, or SEQ ID NO:4 to the animal. In certain embodiments, the animal is a mammal.

In certain embodiments, the present invention provides a method of increasing biogenesis of mitochondria and adaptation of muscle in an animal in need thereof, comprising administering a musclin peptide having at least 80% identity to SEQ ID NO:1, SEQ ID NO:2, SEQ ID NO:3, or SEQ ID NO:4 to the animal. In certain embodiments, the animal is a mammal. In certain embodiments, the present invention provides a musclin peptide having at least 80% identity to SEQ ID NO:1, SEQ ID NO:2, SEQ ID NO:3, or SEQ ID NO:4 for use in medical therapy.

In certain embodiments, the present invention provides the use of a musclin peptide having at least 80% identity to SEQ ID NO:1, SEQ ID NO:2, SEQ ID NO:3, or SEQ ID NO:4 for the manufacture of a medicament useful for increasing muscle growth, performance, resistance to injury and/or preventing or reducing muscle atrophy in an animal. In certain embodiments, the animal is a mammal.

In certain embodiments, the present invention provides a coated device comprising (a) a solid substrate; and (b) a solid composite comprising the musclin peptide having at least 80% identity to SEQ ID NO:1, SEQ ID NO:2, SEQ ID NO:3, or SEQ ID NO:4 in an adherent layer on the solid substrate.

BRIEF DESCRIPTION OF DRAWINGS

FIG. 1A) Representative western blots for musclin and GAPDH in protein extracts from gastrocnemius. Summary statistics for FIG. 1B) musclin protein expression normalized to GAPDH by densitometry of western blots of protein extracts from gastrocnemius, FIG. 1C) tibialis anterior musclin mRNA normalized to HPRT by quantitative rtPCR, and FIG. 1D) musclin peptide expression in plasma by custom ELISA (the y-axis range begins at the lower limit for detection for this assay of 20 pg/ml). FIG. 1E) Representative immunohistochemical stains of gastrocnemius cross sections imaged by confocal microscopy. Red=musclin, green=nuclei. GAPDH: glyceraldehyde 3-phosphate dehydrogenase, HPRT: hypoxanthine guanine phosphoribosyl transferase. $*p<0.05$ vs. control.

FIG. 3A) Representative western blots of Akt, FOXO1 and GAPDH from cultured murine primary myoblasts in 1 mM $Ca^{2+}$ without ionophore (control) vs. with 1 ionophore A23187 (Sigma Aldrich). Summary statistics for phosphorylated Akt (p-Akt) and phosphorylated FOXO1 (p-FOXO1) normalized to FIG. 3B) GAPDH and FIG. 3C) total Akt and total FOXO1, respectively, with (gray) and without (white, control) 1 μM ionophore ($*<0.05$ vs. control). Summary statistics for musclin mRNA normalized to HPRT in FIG. 3D) murine cultured primary myoblasts exposed to various concentrations of ionophore, $Ca^{2+}$ and Akt inhibitor-viii ($*p<0.05$ vs. no ionophore), and FIG. 3E) human cultured primary myoblasts exposed to no $Ca^{2+}$ vs. 1.0 mM $Ca^{2+}$ and various doses of ionophore, by densitometry of western blots ($*p<0.05$ vs.

Ca$^{2+}$-free). Akt: protein kinase B, FOXO1: forkhead box O1, HPRT: hypoxanthine guanine phosphoribosyl transferase.

Figures 4A, 4N:
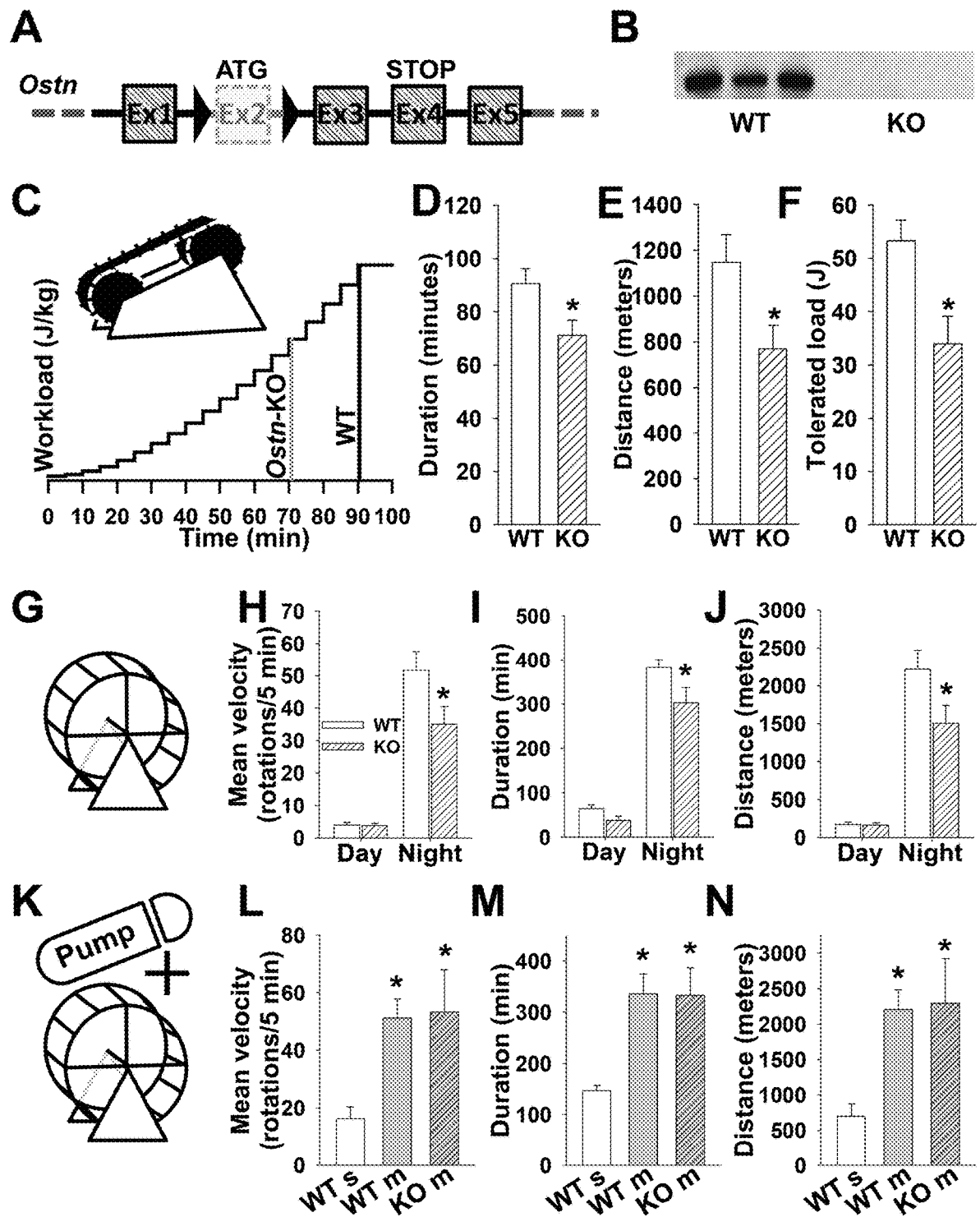

FIGS. 4A-4N. Musclin supports physical performance. FIG. 4A) Schematic of the modified Ostn gene indicating excision of the ATG-containing exon 2 in order to create the Ostn-KO mouse model. FIG. 4B) Representative western blot of musclin from gastrocnemius of WT and Ostn-KO mice. FIG. 4C) Schematic of the treadmill exercise protocol. Vertical lines indicate mean time points of exercise drop-out. Summary statistics for treadmill exercise tolerance in terms of FIG. 4D) duration, FIG. 4E) distance, and FIG. 4F) tolerated work load: $E_k+E_p$ (*p<0.05 Ostn-KO vs. WT). FIG. 4G) Schematic of a running wheel. Summary statistics for voluntary running wheel exercise performance at day and night in terms of FIG. 4H) mean velocity, FIG. 4I) duration, and FIG. 4J) distance (*p<0.05 Ostn-KO vs. WT). FIG. 4K) Schematic of a running wheel and an osmotic pump loaded with musclin (m) or saline (s). Summary statistics for voluntary running wheel performance at night in terms of FIG. 4L) mean velocity, FIG. 4M) duration, and FIG. 4N) distance (*p<0.05 vs. WT Saline). WT: wild-type, KO: Ostn knock out.

Figures 5A, 5B, 5C, 5D, 5E, 5F:
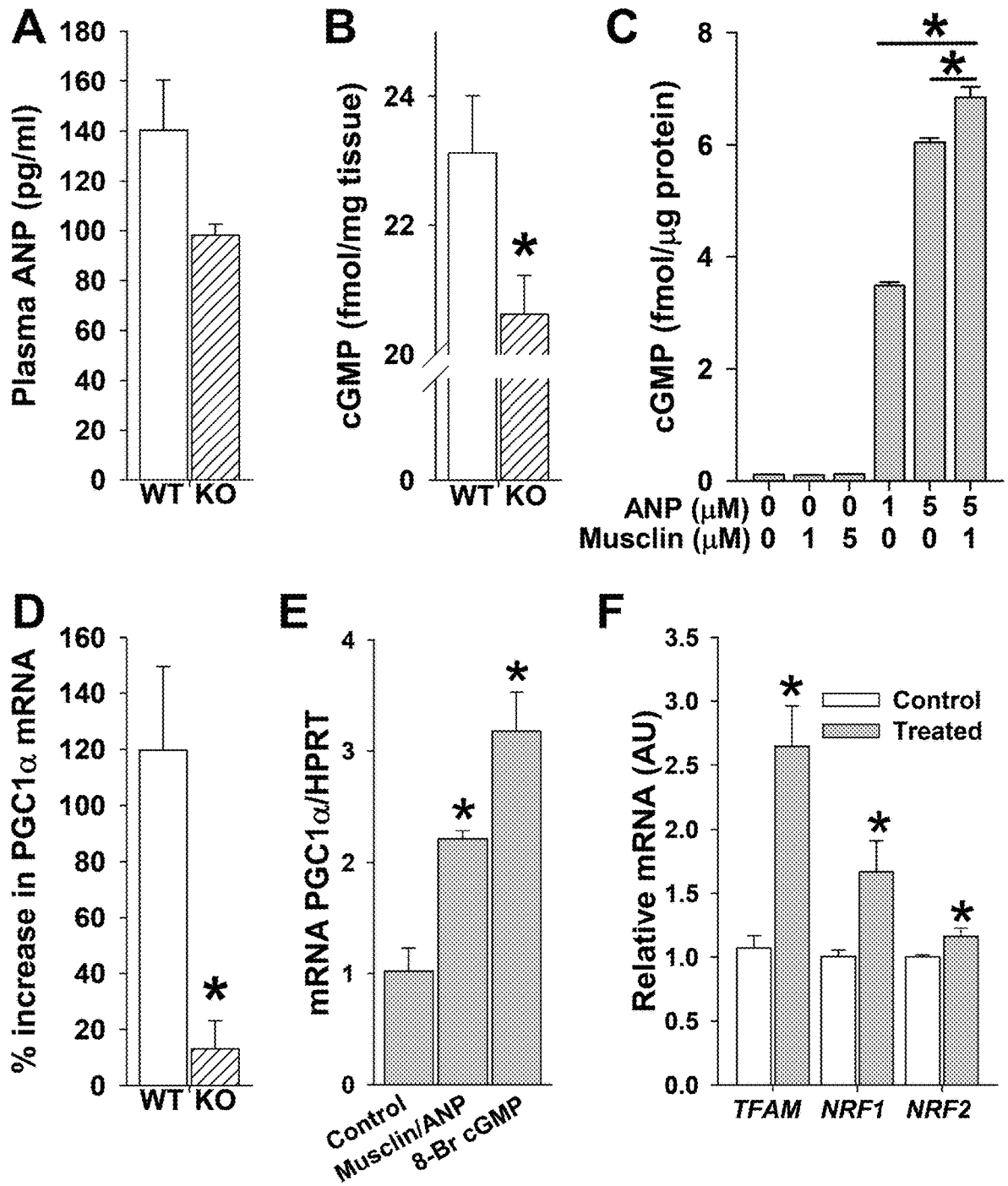

FIGS. 5A-5F. Musclin augments ANP signaling in skeletal muscle. Mice were exercised on a treadmill for 5 d before undergoing assessment of ANP signaling. FIG. 5A) Summary statistics for plasma ANP as assessed by ELISA. FIG. 5B) Summary statistics for cGMP in gastrocnemius by enzyme immunoassay (*p<0.05 Ostn-KO vs. WT). FIG. 5C) Summary statistics for cGMP production in a culture of murine primary myoblasts exposed to various concentrations of ANP and musclin (*p<0.05 vs. columns indicated by bar). FIG. 5D) Summary statistics for % increase in PGC1α mRNA over baseline in response to exercise in tibialis anterior by quantitative rtPCR (p<0.05 vs. WT). ANP: atrial natriuretic peptide, WT: wild-type, KO: Ostn knock out, cGMP: cyclic guanosine monophosphate. FIG. 5E. Summary statistics for primary myoblast culture mRNA of PGC1-α normalized to HPRT in response to musclin/ANP or to 8-Br-c-GMP. FIG. 5F. Summary statistics for primary myoblast culture relative mRNA of TFAM, NRF1, and NRF2 with and without musclin/ANP. KO, Ostn-KO.

Figures 6A, 6B, 6C, 6D, 6E, 6F, 6G:
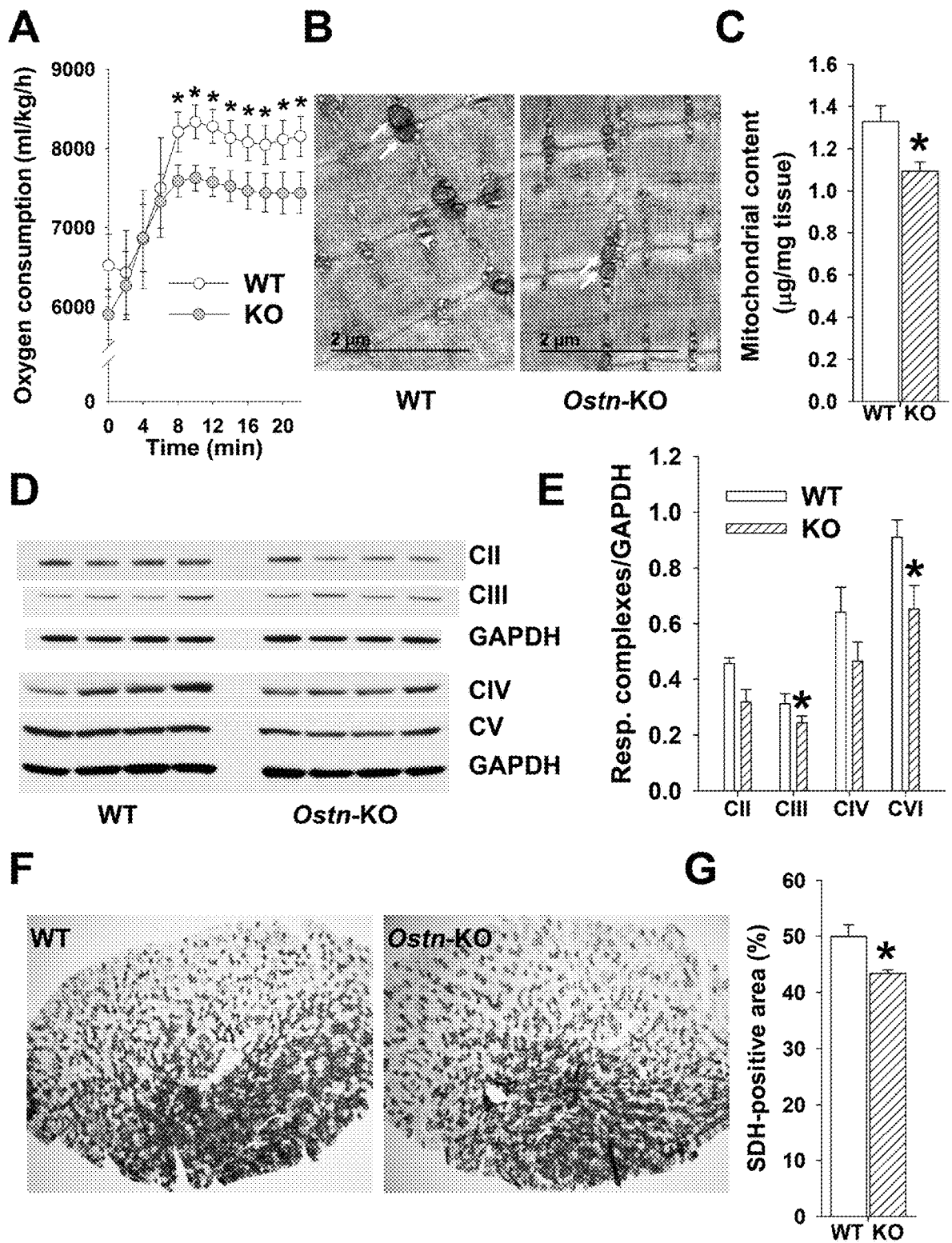
Figures 7A, 7B, 7C, 7D:
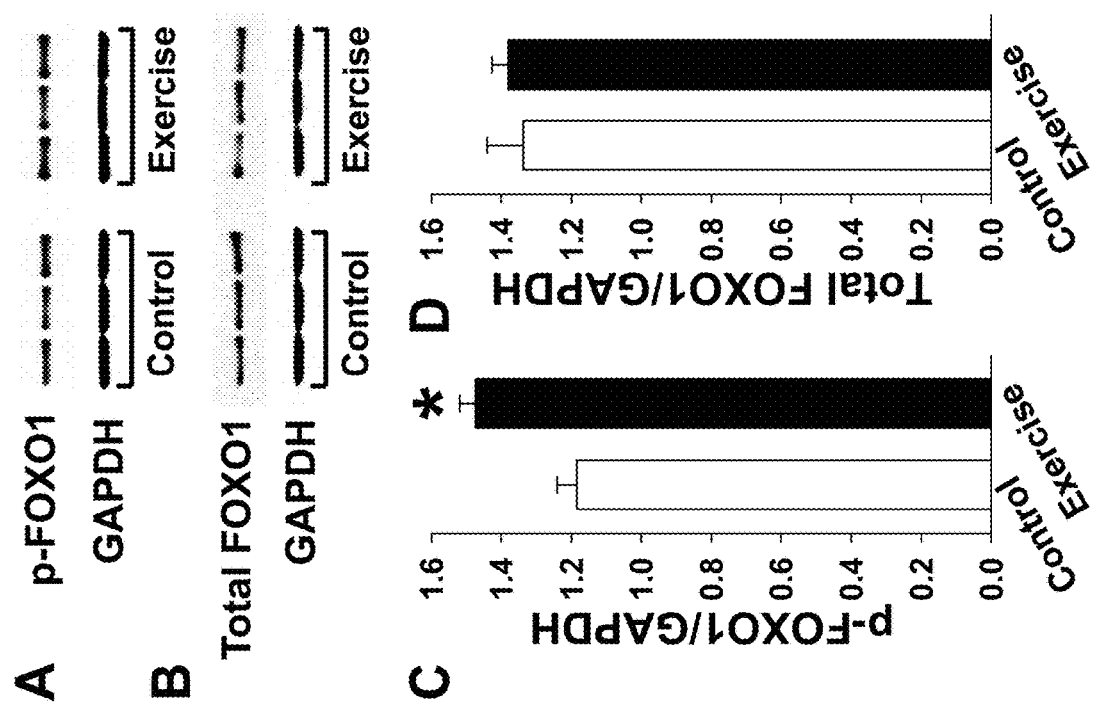
Figures 8A, 8B, 8C, 8D:
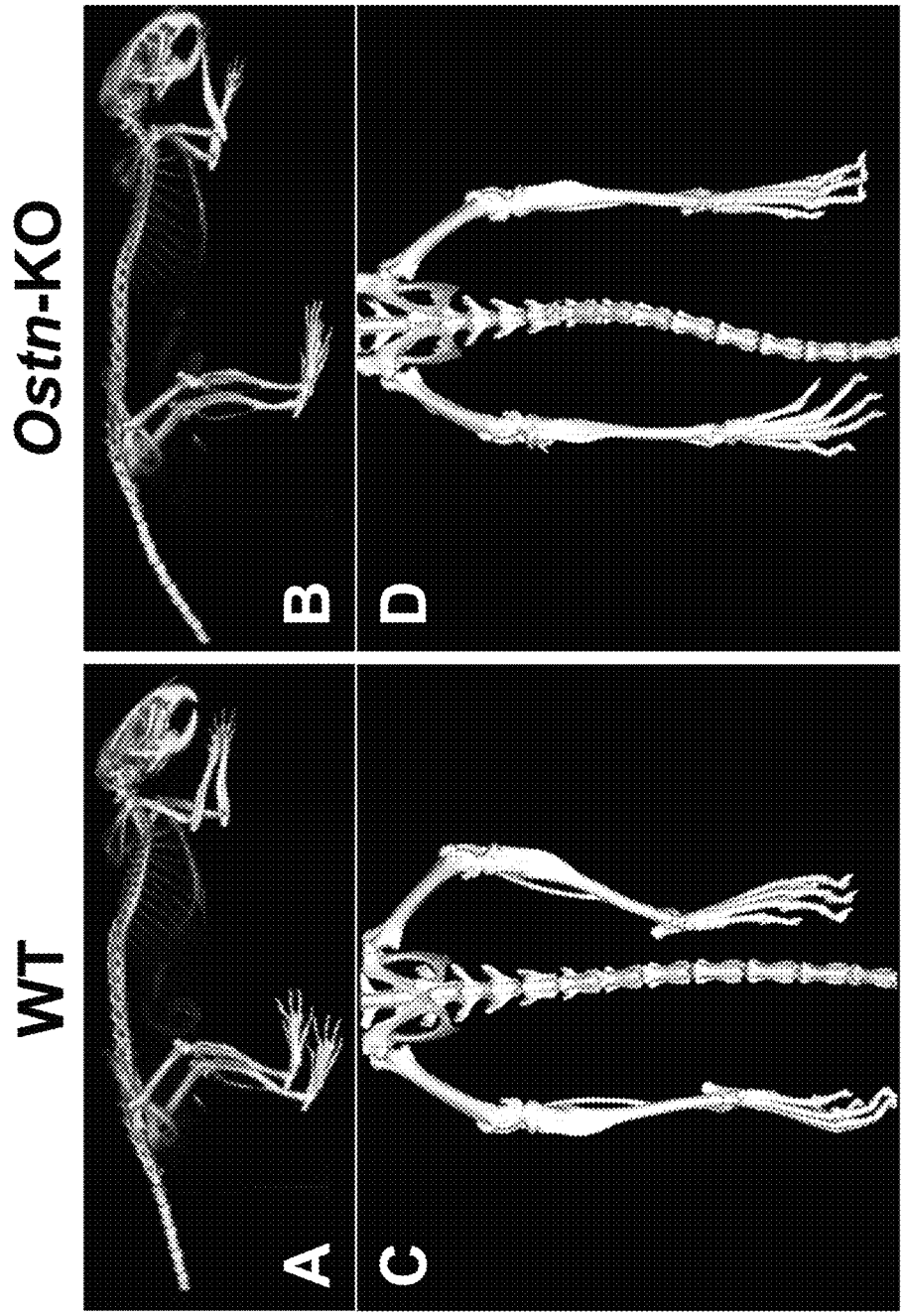

FIGS. 6A-6G. Musclin signaling improves aerobic capacity and prompts mitochondrial biogenesis. FIG. 6A) Summary statistics for trend of oxygen consumption over time of exercise-trained mice upon initiation of treadmill exercise at time 0 (*p<0.05 vs. Ostn-KO). FIG. 6B) Representative electron micrographs of longitudinal tibialis anterior sections from exercised mice. White arrows indicate mitochondria. FIG. 6C) Summary statistics for mitochondrial content by weight in gastrocnemius isolates of exercised mice (*p<0.05 vs. WT). FIG. 6D) Representative western blots of respiratory chain enzymes and GAPDH and FIG. 6E) summary statistics for respiratory complex expression normalized to GAPDH in gastrocnemius of exercise-trained mice (*<0.05 vs. WT). FIG. 6F) Representative stains for SDH activity of tibialis anterior cross sections and FIG. 6G) summary statistics for % area of cross sections stained for SDH activity in exercise-trained mice (*p<0.05 vs. WT). WT: wild-type, KO: Ostn knock out, GAPDH: glyceraldehyde 3-phosphate dehydrogenase, SDH: succinate dehydrogenase.

FIGS. 7A-7D. Exercise increases FOXO1 phosphorylation. Representative western blots of A) phosphorylated FOXO1 (p-FOXO1) and B) total FOXO1 as well as corresponding GAPDH in gastrocnemius muscle of exercised and non-exercised (control) mice. Summary statistics for C) phosphorylated FOXO1 and D) total FOXO1 normalized to GAPDH (*p<0.05 vs. sedentary control). FOXO1: forkhead box O1 transcription factor, GAPDH: glyceraldehyde 3-phosphate dehydrogenase.

FIGS. 8A-8D. Skeletal structure is grossly intact in Ostn-KO. Representative projections of high-resolution computed tomography (CT) 3-D reconstruction of the skeletons of A) WT and B) Ostn-KO mice, with enlarged views of the lower extremities of C) WT and D) Ostn-KO mice.

Figure 9:
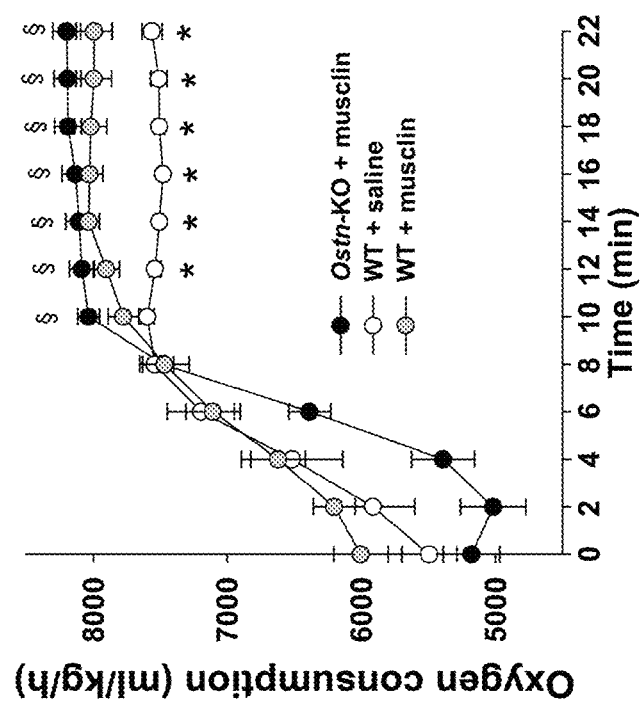

FIG. 9. Oxygen consumption of Ostn-KO is rescued by musclin infusion. The oxygen consumption, $VO_2$, over time upon initiation of treadmill exercise was compared in WT and Ostn-KO mice treated with 3 weeks of saline or musclin delivered by osmotic pump. Oxygen consumption of WT mice treated with musclin was slightly better for several time points than that of WT mice treated with saline. Oxygen consumption of Ostn-KO mice treated with musclin is equivalent to that of WT mice treated with musclin and was better than WT treated with saline once steady state was achieved (*p<0.05 for WT+musclin vs. WT+saline, § p<0.05 for Ostn-KO+musclin vs. WT+saline). Ostn-KO: Ostn knock out, WT: wild type.

Figures 10A, 10B:
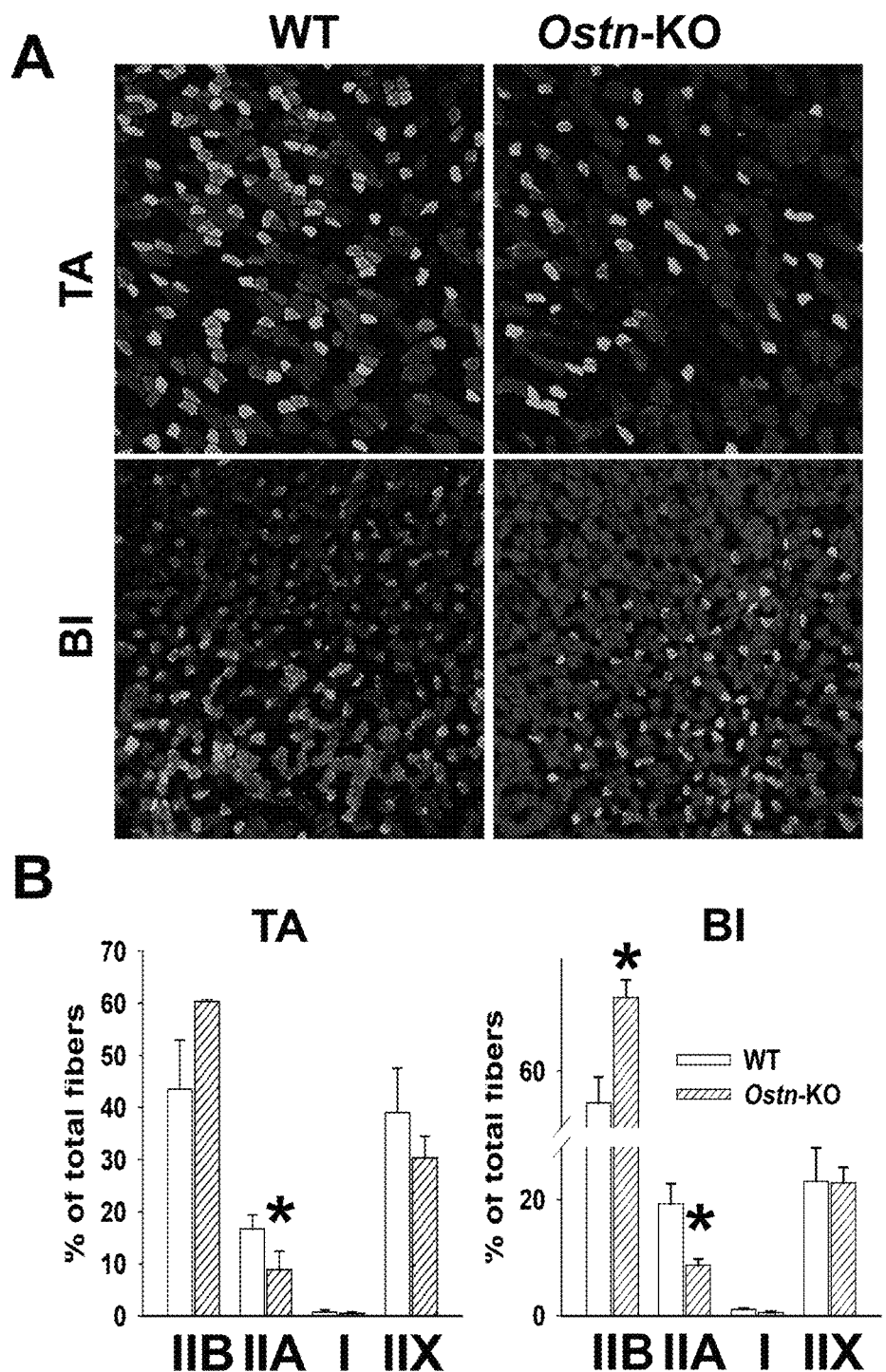
Figures 11A, 11B, 11C, 11D, 11E, 11F, 11G:
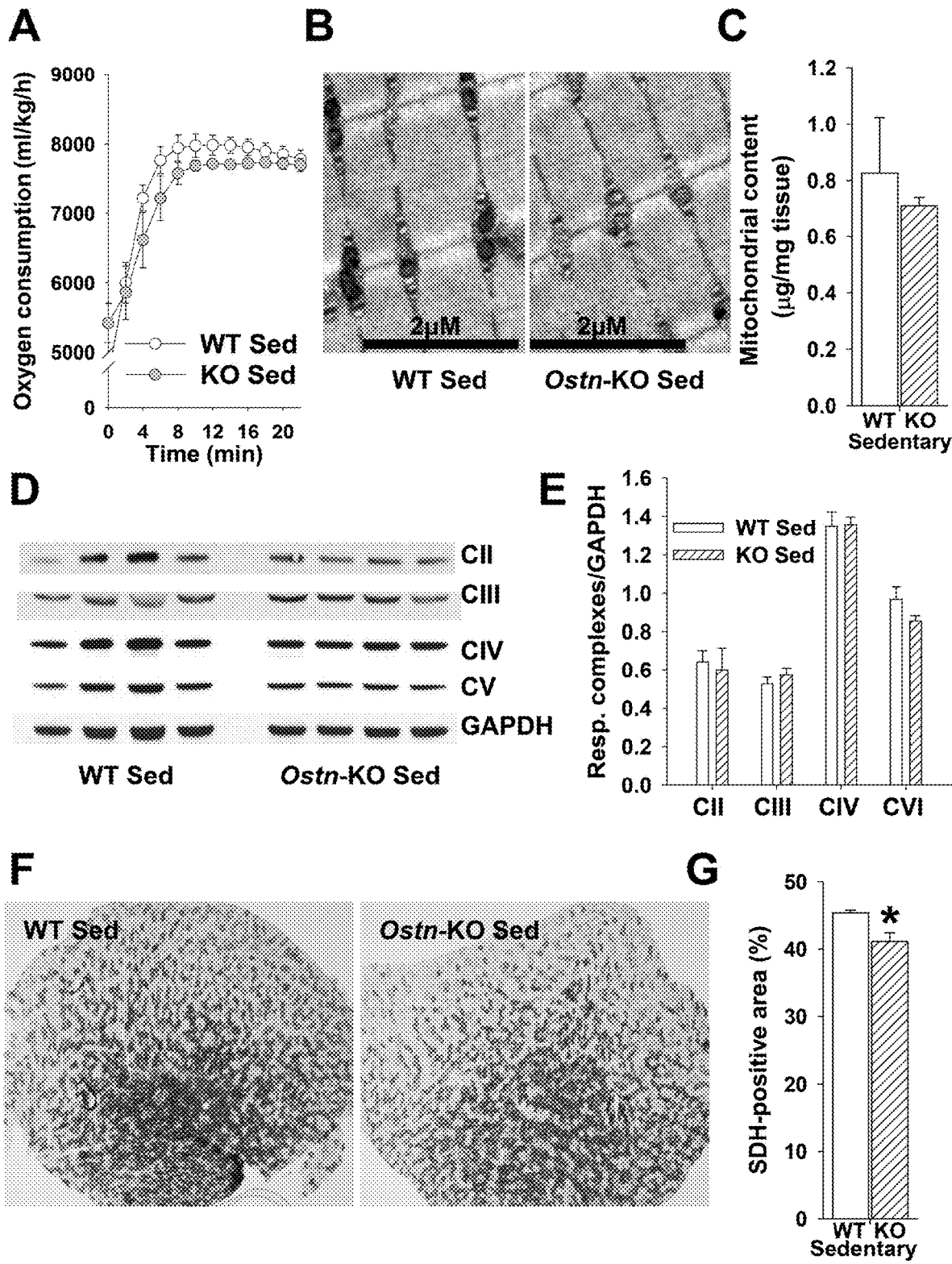

FIGS. 10A-10B. Musclin controls skeletal muscle fiber type. A) Representative immunohistochemical stains for fiber type in cross sections of biceps femoris and tibialis anterior of exercise-trained WT and Ostn-KO mice. Red=IIB, green=IIA, blue=I, and black=IIX staining. B) Summary statistics for fiber type as assessed by counting # of stained fibers per field (*p<0.05 vs. WT). WT: wild type, Ostn-KO: Ostn knock out, TA: tibialis anterior, BI: biceps femoris.

FIGS. 11A-11G: Differences in aerobic capacity and markers of mitochondrial biogenesis are minimal in sedentary WT and Ostn-KO mice. A) Summary statistics for trend of oxygen consumption over time of sedentary WT and Ostn-KO mice upon initiation of treadmill exercise at time 0 (all points NS for WT vs. Ostn-KO). B) Representative electron micrographs of longitudinal tibialis anterior sections from sedentary mice. C) Summary statistics for mitochondrial content by weight in gastrocnemius isolates of sedentary mice (*p<0.05 vs. WT). D) Representative western blots of respiratory chain enzymes and GAPDH and E) summary statistics for respiratory complex expression normalized to GAPDH in gastrocnemius of sedentary WT and Ostn-KO mice. F) Representative stains for SDH activity of tibialis anterior cross sections and G) summary statistics for % area of cross sections stained for SDH activity in sedentary WT and Ostn-KO mice (*p<0.05 vs. WT). WT: wild-type, KO: Ostn knock out, Sed: sedentary, GAPDH: glyceraldehyde 3-phosphate dehydrogenase, SDH: succinate dehydrogenase.

Figure 12:
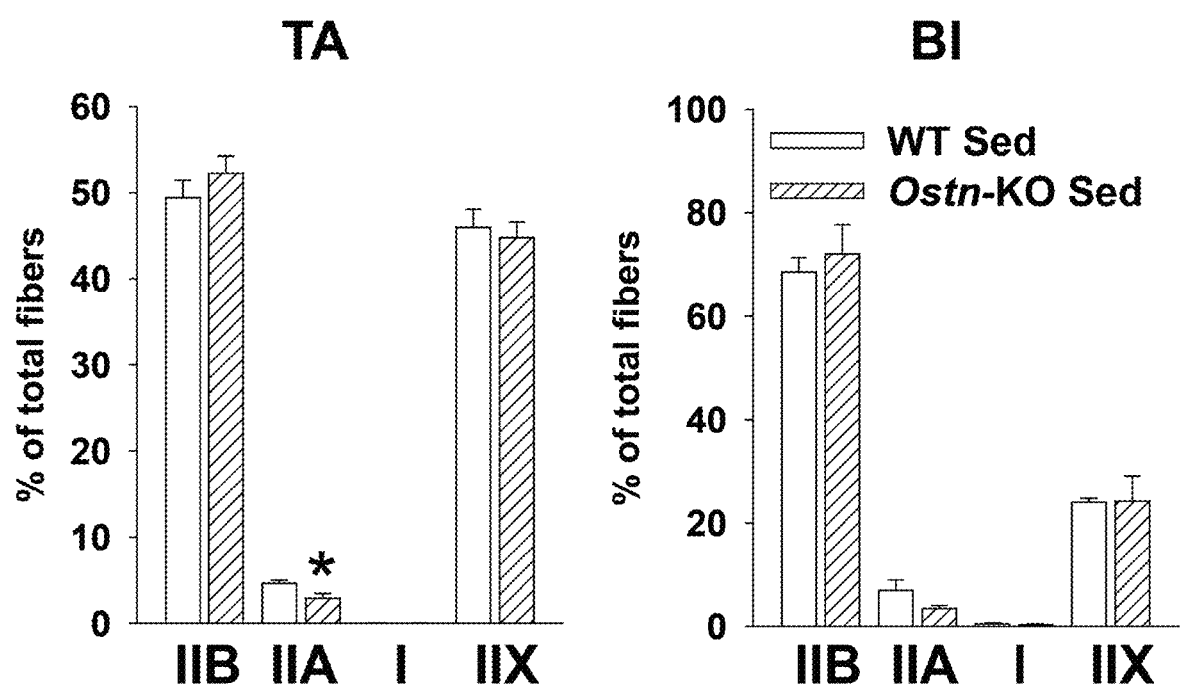

FIG. 12. Differences in skeletal muscle fiber type are less marked in sedentary WT vs. Ostn-KO mice. Summary statistics for fiber type as assessed by counting # of stained fibers per field in tibialis anterior (left) and biceps femoris (right) of sedentary WT and Ostn-KO mice (*p<0.05 vs. WT). WT: wild type, Ostn-KO: Ostn knock out, TA: tibialis anterior, BI: biceps femoris.

Figures 13A, 13B, 13C:
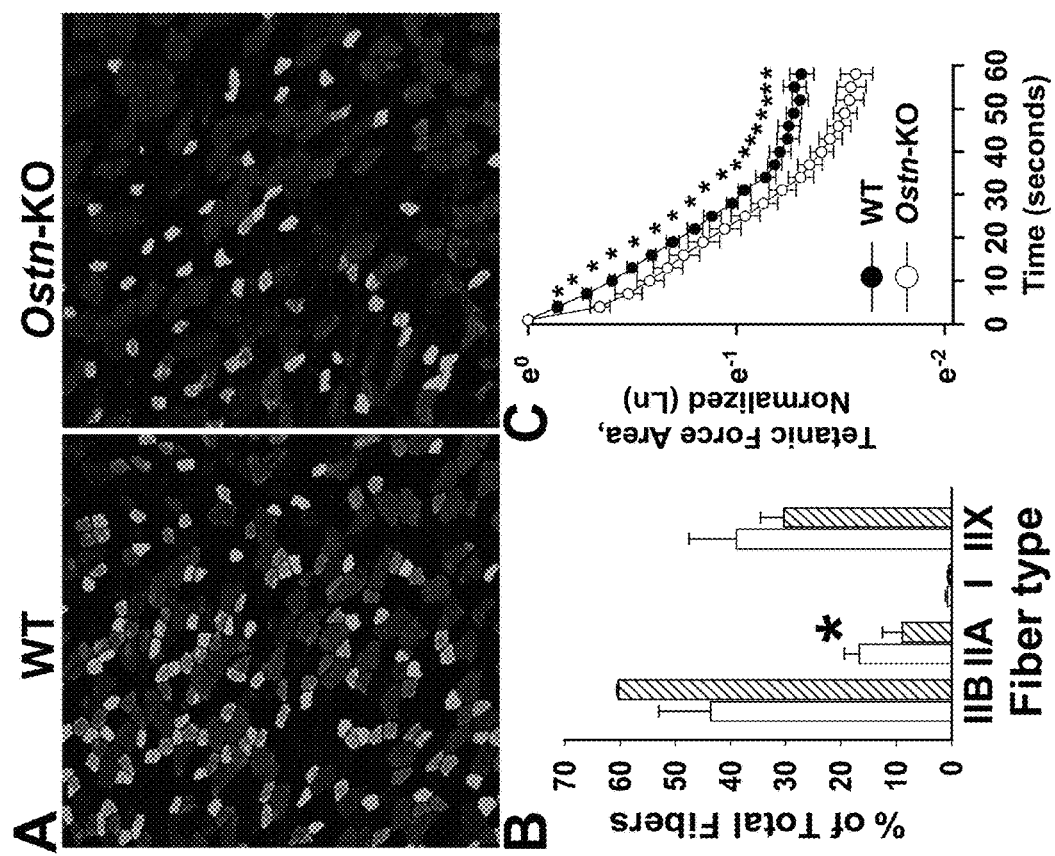

FIGS. 13A-13C. Musclin-dependent fiber type shift and fatigue tolerance in exercise-trained mice. A) Representative TA sections stained with red, IIB; green IIA; blue, I; black, IIX. B) Summary of WT vs. Ostn-KO TA fiber types: JIB 43.1±9.6 vs. 6.05±0.4, IIA 16.4±3 vs. 8.5±4.2, I 1.1±0.05 vs. 0.7±0.03, IIX 39.0±9.1 vs. 32.2±3.6, n=4 each (Subbotina et al., PNAS, 2015). C) TA fatigue by area under tetanic force curve, n=4 each. *p<0.05.

Figures 14A, 14B:
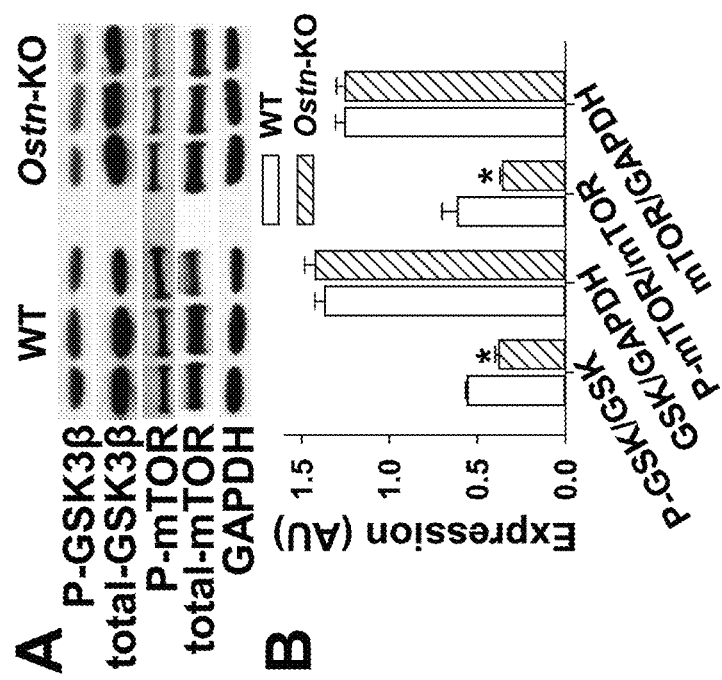

FIGS. 14A-14B. Downstream musclin targets. A) Western blots of phosphorylated and total GSK3β and mTOR in trained WT vs. Ostn-KO. B) Summary statistics: 0.56±0.01 vs. 0.38±0.02 for P-GSK/total GSK, 1.37±0.06 vs. 1.42±0.06 for total GSK/GAPDH, 0.61±0.09 vs. 0.36±0.02 for P-mTOR/total mTOR, 1.25±0.05 vs. 1.25±0.05 for total mTOR/GAPDH, for WT vs. Ostn-KO, respectively, n=3 each, $*p<0.05$.

Figures 15A, 15B:
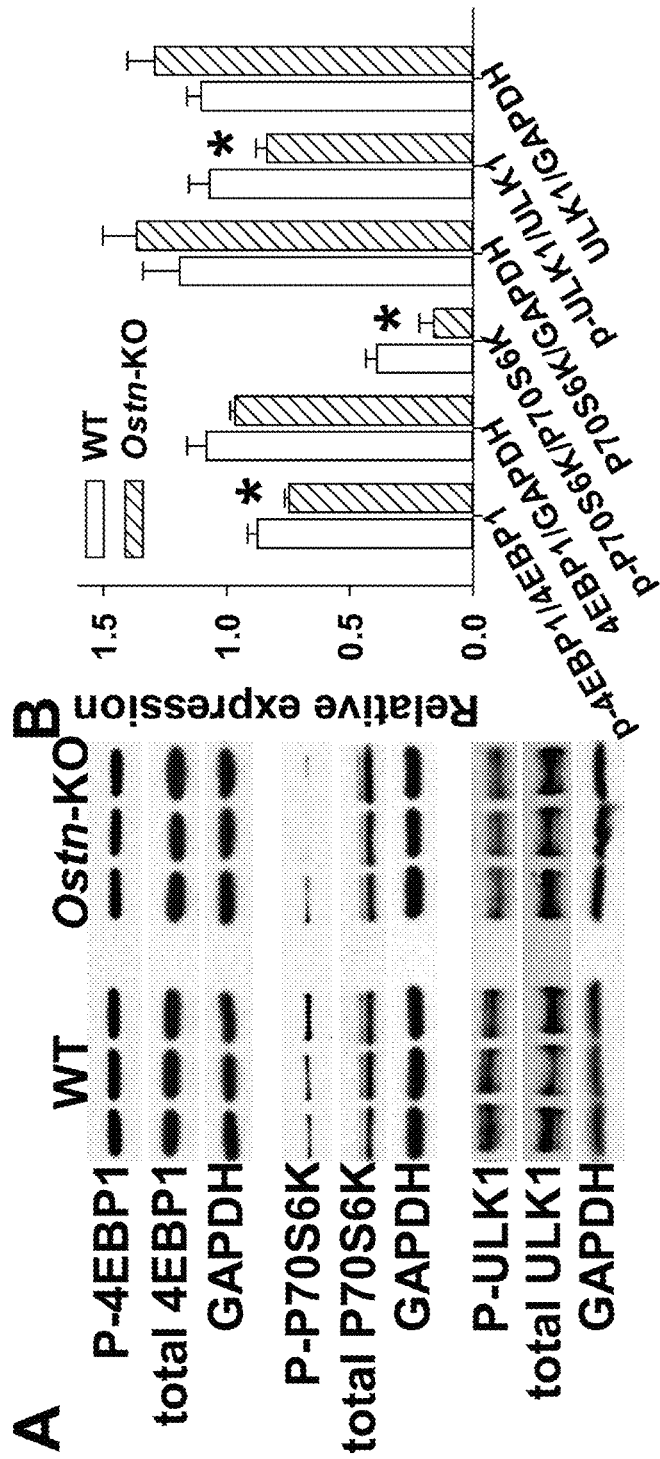
Figures 16A, 16B, 16C, 16D, 16E, 16F, 16G:
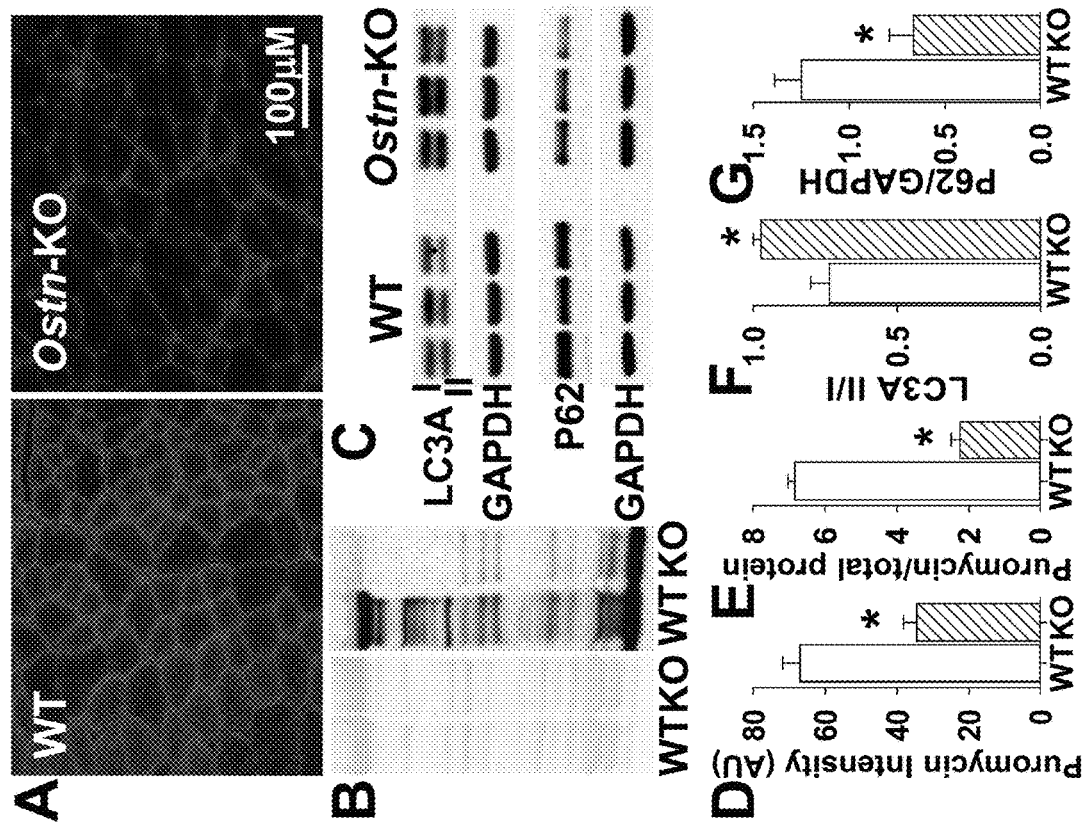

FIGS. 15A-15B. Phosphorylation of mTOR targets. A) Representative western blots. B) Summary statistics: 0.88±0.04 vs. 0.75±0.02 p-4EBP1/total 4EBP1, 1.08±0.08 vs. 0.97±0.02 4EBP1/GAPDH, 0.39±0.04 vs. 0.16±0.06 p-P70S6K/total P70S6K, 1.19±0.15 vs. 1.37±0.14 p-P70S6K/GAPDH, 1.07±0.08 vs. 0.84±0.04 p-ULK1/total ULK1, 1.10±0.06 vs. 1.29±0.110 ULK1/GAPDH, n=3 each, $*p<0.05$.

FIGS. 16A-16G. Muscle protein synthesis and autophagy. A) TA cross sections stained for puromycin incorporation. B) Representative gel and western blot for puromycin. C) Representative western blots for autophagy markers and respective GAPDH. WT vs. Ostn-KO quantification of D) puromycin IHC staining (67.0±4.9, n=5 vs. 34.6±3.7, n=6 AU), E) puromycin by western blot (6.84±0.19 vs. 2.25±0.24, n=2 each), F) LC3AII/I (0.74±0.06 vs. 0.97±0.03, n=3 each), G) P62 expression (1.25±0.14 vs. 0.67±0.13, n=4 each), $*p<0.05$.

Figures 17A, 17B:
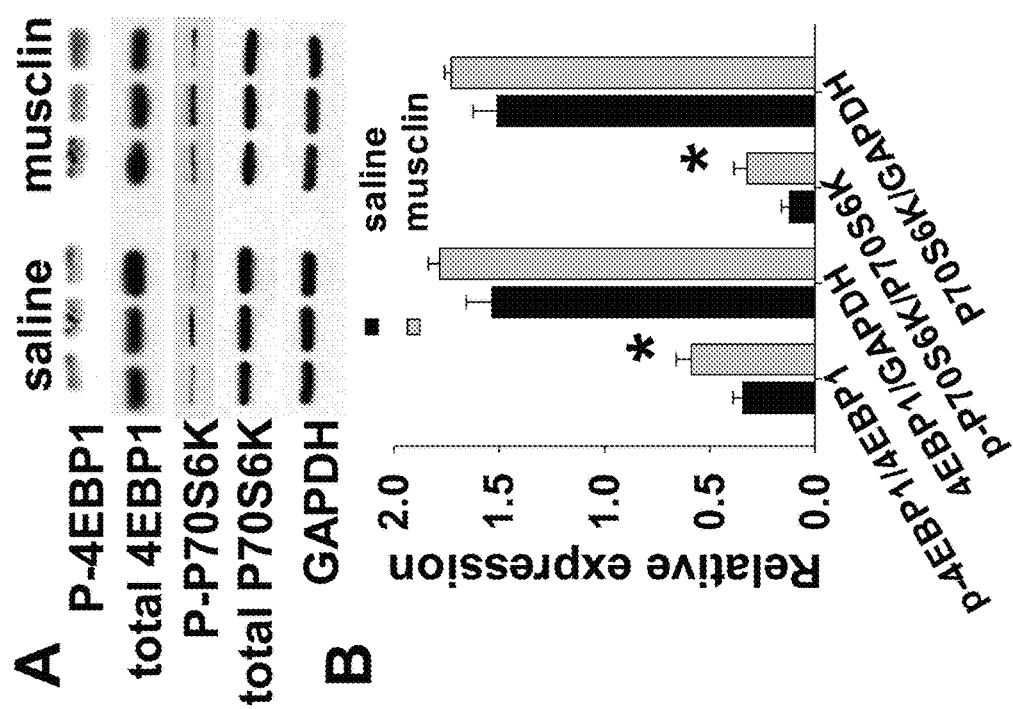

FIGS. 17A-17B. Phosphorylation of mTOR targets is upregulated by musclin infusion. Summary statistics of relative expression of phosphorylated vs. total proteins and total proteins vs. GAPDH from western blots: 0.34±0.05 vs. 0.59±0.07 p-4EBP1/total 4EBP1, 1.53±0.12 vs. 1.78±0.05 4EBP1/GAPDH, 0.12±0.04 vs. 0.32±0.06 p-P70S6K/total P70S6K, 1.51±0.12 vs. 1.73±0.03 P70S6K/GAPDH for saline vs. musclin respectively, n=3 each, $*p<0.05$ saline vs. musclin.

FIGS. 18A-18D. Musclin-dependent OPA1 expression and vulnerability to apoptosis. A) Western blots from GCN. B) Summary expression data for WT and Ostn-KO muscle (1.47±0.08 vs. 0.96±0.14 for OPA1, 0.61±0.05 vs. 0.63±0.04 for mitofusin, n=4 each). C) Summary data of OPA1 mRNA normalized to HPRT by PCR in myotube culture exposed to musclin (1.04±0.28 for no peptides, n=2, 4.21±0.24 for ANP 5 µM, n=3, 5.19±0.05 for ANP 5 µM+musclin 1 µM, n=3, 5.61±0.36 for 8-Br-cGMP 100 mM, n=3). D) Summary data for TUNEL staining in GCN of WT vs. Ostn-KO after eccentric exercise (23.21±4.56, n=8 vs. 36.46±2.51, n=6 each). $*p<0.05$.

FIGS. 19A-19E. Muscle weight and fiber size after fasting/refeeding. Summary data for A) plasma musclin in WT mice at the end of 48 h fast vs. 4 h after refeeding (27.71±5.5, n=3 vs. 46.24±4.6 pg/ml, n=6). Muscle weight in WT and Ostn-KO mice 4 h after relief of 48 h fast (n=5 each) for B) GCN (76.25±1.12 vs. 72.23±1.13) and C) QFM (85.40±1.47 vs. 77.31±1.66). D) Representative H&E of TA cross sections obtained 4 h after relief of 48 h fast illustrating fiber size. E) Summary data for TA fiber area 4 h after refeeding from 48 h fast (195.8±8.7, n=14 vs. 119.4±6.0 µm$^2$, n=17). $*p<0.05$ FIGS. 20A-20B. mTOR targets after refeeding. A) Western blots of mTOR targets and GAPDH. B) Relative expression: 0.57±0.04 vs. 0.39±0.01 p-4EBP/total 4EBP, 1.31±0.01 vs. 1.25±0.06 total 4EBP/GAPDH, 0.81±0.04 vs. 0.20±0.02 p-P70/total P70, 2.14±0.18 vs. 2.28±0.23 total P70/GAPDH, 1.24±0.36 vs. 0.22±0.07 p-ULK1/total ULK1, 0.57±0.03 vs. 0.83±0.19 total ULK1/GAPDH, for WT and Ostn-KO respectively, n=3 each, $*p<0.05$.

DETAILED DESCRIPTION

Skeletal muscle is increasingly recognized as a secretory organ. Revealing the identity and function of myokines can improve the understanding of skeletal muscle function under sedentary or exercise conditions, as well as its coordination with other organs, tissues and overall body metabolism. The present inventors identified musclin (also called osteocrin or bone peptide-1) as an exercise-responsive myokine critical for skeletal muscle adaptation to physical activity. They developed a new Ostn knock-out mouse, which allowed the determination of a previously unrecognized physiologic function of musclin in regulation of skeletal muscle mitochondrial biogenesis and physical endurance. They demonstrated a molecular mechanism for musclin-dependent skeletal muscle adaptation to exercise that also transforms the perspective on natriuretic peptide signaling, particularly as relates to physical activity and exercise-induced remodeling in different tissues.

Musclin is a protein that is produced by skeletal muscles. The present inventors showed that skeletal muscles increase their production of this protein in response to exercise and that this protein causes skeletal muscles to adapt their molecular composition so that they are less susceptible to fatigue. It was discovered that sections of the musclin protein can be synthesized and given to animals as an infusion and that this infusion improved voluntary exercise performance, and changed the way muscles utilize oxygen. The data presented herein also indicate that musclin reduced muscle injury and improved the retention of muscle that is otherwise lost or atrophied following limited nutrition.

The present invention uses musclin as a preventative or therapeutic agent. Its potential use includes enhancement of exercise performance in both healthy subjects and to rehabilitate subjects after disease or injury, to limit injury to muscle under noxious stressors such as may be caused by overuse, poor blood flow or toxic medication, and to preserve or restore muscle mass when it would otherwise be lost due to insufficient mobility, such as in patients hospitalized and bedbound with severe illness or injuries, during space flight, in spinal cord or nerve injuries when the stimulation of muscle contractions is reduced, and in response to aging.

The present invention has applications in both human and veterinary situations. For example, the musclin peptide can be administered to an animal, such as a mammal. In certain embodiments, the mammals can be humans, pets (such as dogs or cats), horses, or other mammals.

It has been observed that patients can lose a significant amount to muscle mass due to inactivity or stress. For example, if a patient needs to immobilize a limb in a cast due to a broken bone, the patient can lose about 30% of the muscle mass in the limb. Also, surgical patients can lose muscle mass due to forced inactivity after a procedure. Further, loss of muscle mass is seen in elderly individuals, which can result in functional level difficulties, which can then exacerbate the problem, as they lose mobility.

The inventors have determined that beneficial muscle adaptation to exercise or stress can be driven by the stimulation of an anabolic shift in the balance between protein synthesis and breakdown promoted by the skeletal muscle-produced peptide musclin. Musclin, therefore, can be used to promote endurance and trainability by healthy and ill or disabled people and animals. Further, the inventors have found that musclin signaling underlies exercise-induced upregulation of the optic atrophy 1 (OPA1) protein that protects against muscle fiber damage by apoptosis in response to excessive loads. Thus, musclin can also be used for prevention of muscle loss under conditions where apoptosis is an important mediator of muscle fiber pathology, such as physical activity when applied without proper training, statin-induced myopathy, sympathetic over-stimulation and peripheral vascular disease with limb ischemia. Also, skeletal muscles serve as the largest bodily protein reservoir and source of amino acids for gluconeogenesis and energy production during catabolic states, including those related to illness, injury, immobility and inadequate nutrition. However, excessive protein degradation and muscle loss are associated with poor recovery and increased risk of mortality. The data indicate that musclin can serve a protective role in preservation or restoration of muscle mass and function after catabolic stress. Given that muscle loss from catabolic stress is very common in hospitalized patients with any severe illness or major surgeries, musclin can be used to support muscle recovery under these circumstances in both humans and animals. Finally, it has been found that musclin can influence signaling by atrial natriuretic peptide (ANP), a powerful exercise-responsive regulator of metabolism in numerous tissues, and this property can be employed for promotion of overall skeletal muscle, metabolic and cardiovascular health and function.

Musclin Peptide

```
The full-length human musclin peptide has the
following amino acid sequence (SEQ ID NO: 1:
SFSGFGSPLDRLSAGSVDHKGKQRKVVDHPKRRFGIPMDRIGRNR
LSNSRG.

A truncated human musclin peptide has the
following amino acid sequence (SEQ ID NO: 2:
SFSGFGSPLDRLSAGSVDHKGKQRKVVDHPKRR.

The full-length mouse musclin peptide has the
following amino acid sequence (SEQ ID NO: 3:
SFSGFGSPLDRLSAGSVEHRGKQRKAVDHSKKRFGIPMDRIGRNR
LSSSRG.

A truncated mouse musclin peptide has the
following amino acid sequence (SEQ ID NO: 4:
SFSGFGSPLDRLSAGSVEHRGKQRKAVDHSKKR.
```

In certain embodiments, the musclin peptide comprises at least 80% identity to one of SEQ ID NO: 1-4. In certain embodiments, the musclin peptide has 80%, 81%, 82%, 83%, 84%, 85%, 86%, 87%, 88%, 89%, 90%, 91%, 92%, 93%, 94%, 95%, 96%, 97%, 98%, 99% or 100% identity to one of SEQ ID NO: 1-4.

In certain embodiments, the musclin peptide has at least 80% identity to SEQ ID NO:2.

In certain embodiments, the musclin peptide has 100% identity to SEQ ID NO:2.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

The term "peptide" describes a sequence of 20 to 60 amino acids or peptidyl residues. Preferably a peptide comprises 20 to 40, or 30 to 35 or 33 amino acids. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

The terms "protein," "peptide" and "polypeptide" are used interchangeably herein.

By "variant" peptide is intended a peptide derived from the native peptide by deletion (so-called truncation) or addition of one or more amino acids to the N-terminal and/or C-terminal end of the native peptide; deletion or addition of one or more amino acids at one or more sites in the native peptide; or substitution of one or more amino acids at one or more sites in the native peptide. The peptides of the invention may be altered in various ways including amino acid substitutions, deletions, truncations, and insertions. Methods for such manipulations are generally known in the art. For example, amino acid sequence variants of the peptides can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains. Generally, amino acid sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 8'7%, 88%, 89%, 90%, 91%, 92%, 93%, 94%, 95%, 96%, 97%, to 98%, sequence identity to the native (endogenous) amino acid sequence.

Compositions and Methods of Use

The present invention provides a therapeutic method for preventing or treating a pathological condition or symptom in an animal, such as a mammal. In certain embodiments, the mammal is a human, wherein an increase of muscle mass, growth, performance, resistance to injury and/or atrophy is desired, by administering to an animal in need of such therapy, an effective amount of a musclin peptide. In certain embodiments, the animal is a mammal.

In certain embodiments, the therapeutic composition contains a musclin peptide and a hormone, such as insulin-like growth factor, or natriuretic peptides such as ANP In certain embodiments, the musclin peptide is administered after a medical procedure or stress-inducing event.

In certain embodiments, the musclin peptide is administered after the animal has fasted for more than 6 hours.

In certain embodiments, the musclin peptide is administered about an hour before or an hour after ingesting food.

In certain embodiments, the musclin peptide is administered prior to a medical procedure or stress-inducing event.

In certain embodiments, the animal is a human, dog, cat, or horse.

The present invention provides a musclin peptide for use in medical therapy.

The present invention provides the use of a musclin peptide for the manufacture of a medicament useful for the treatment of a pathological condition or symptom in a mammal, wherein an increase of muscle mass, growth, performance, resistance to injury and/or atrophy is desired.

The musclin peptides can be formulated as pharmaceutical compositions and administered to an animal host, such as a human patient, in a variety of forms adapted to the chosen route of administration, e.g., by subcutaneous injection/infusion or by means of an osmotic pump. In certain embodiments, the pharmaceutical composition is administered subcutaneously, intramuscularly, subfascia, intravenously, intra-fat, peritoneal, inhaled, by infusion pump, transdermally, intradermally, orally, or rectally.

In certain embodiments, the pharmaceutical composition is incorporated into sustained-release preparations and/or on devices.

Solutions of the pharmaceutical compositions containing musclin peptides can be prepared in water or saline, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active ingredient in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of musclin peptide can be determined by comparing their in vitro activity, and in vivo activity in animal models. Methods for the extrapolation of effective dosages in mice, and other animals, to humans are known to the art; for example, see U.S. Pat. No. 4,938,949.

The amount of the musclin peptide required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 microgram/kg/day to about 0.1 mg/kg/day.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple subcutaneous injections.

Musclin peptides of the invention can also be administered in combination with other therapeutic agents, for example, a hormone, such as a growth hormone. Examples of such growth hormones include insulin-like growth factor, or natriuretic peptides such as ANP. Accordingly, in one embodiment the invention also provides a composition comprising a musclin peptide, at least one other therapeutic agent, and a pharmaceutically acceptable diluent or carrier. The invention also provides a kit comprising a musclin peptide, at least one other therapeutic agent, packaging material, and instructions for administering the musclin peptide and the other therapeutic agent or agents to an animal.

Solid Substrates

The present invention further provides a coated device that includes (a) a solid substrate; and (b) a therapeutic substance in an adherent layer on the solid substrate. In certain embodiments, the solid substrate has a metal surface, or a polymeric surface. In certain embodiments, the solid composite includes a plurality of layers. In certain embodiments, the polymer is a biostable polymer. In certain embodiments, the polymer is a silicone, polyurethane, polyester, vinyl homopolymer or copolymer, acrylate homopolymer or copolymer, polyether or cellulosic, or a combination thereof.

Examples of various polymers used in forming the agent-eluting component include poly(methyl(meth)acrylate ("PMMA"), ethylenevinylalcohol ("EVAL"), poly(butyl (meth)acrylate) ("PBMA"), biodegradable polymers (i.e., Poly(glycolic acid) ("PGA") and poly(L-lactic acid) ("PLLA"), polyethylene glycol ("PEG"), hyaluronic acid ("HA"), polyester amide ("PEA"), poly(glycerol-sebacate) ("PGS"), nanoscale structures of carbon, acetal copolymer, acetal homopolymer, acrylonitrile butadiene styrene, ABS and polycarbonate, nylon, polyamide, polyacrylate, polyaryl sulfone, polycarbonate, polyetherketone, polyetherimide, polyether sulfone, polyethylene terephthalate, polyimide, polyphenylene oxide, polyphenylene sulfide, polypropylene, polysulfone, polyurethane, polyvinyl chloride, styrene acrylonitrile and other suitable polymers. It is contemplated that the above polymers can be slowly dissolved or chemically degraded or both. The local drug-eluting component alternatively may be fabricated from porous ceramic or various metals or alloys, including stainless steel, platinum, titanium, tantalum, nickel-titanium, cobalt-chromium, and alloys thereof. This family of polymers comprises the following basic components: (1) moieties derived from aliphatic diols, triols, or polyols; (2) moieties derived from polycarboxylic acids (carboxylic acids containing more than one acid functionality); and (3) biobeneficial, non-fouling, or bioactive moieties (U.S. Pat. No. 7,186,789, incorporated by reference herein).

In certain embodiments, the present invention provides a coated device comprising: (a) a solid substrate; and (b) a solid composite comprising the musclin peptide having at least 80% identity to SEQ ID NO:1, SEQ ID NO:2, SEQ ID NO:3, or SEQ ID NO:4 in an adherent layer on the solid substrate. In certain embodiments, the solid substrate has a metal surface. In certain embodiments, the solid substrate has a polymeric surface.

The invention will now be illustrated by the following non-limiting Examples.

Example 1

Musclin is an Activity-Stimulated Myokine that Enhances Physical Endurance

Exercise remains the most effective way to promote physical and metabolic wellbeing, but molecular mechanisms underlying exercise tolerance and its plasticity are only partially understood. In this study, musclin—a peptide with high homology to natriuretic peptides (NP)— was identified as an exercise-responsive myokine that acts to enhance exercise capacity in mice. Human primary myoblast culture and in vivo murine models were used to establish that the activity-related production of musclin is driven by $Ca^{2+}$-dependent activation of Akt1 and the release of musclin encoding gene (Ostn) transcription from forkhead box O1 (FOXO1) inhibition. Disruption of Ostn and elimination of musclin secretion in mice resulted in reduced exercise tolerance that can be rescued by treatment with recombinant musclin. Reduced exercise capacity in mice with disrupted musclin signaling was associated with a trend toward lower levels of plasma atrial natriuretic peptide (ANP) and significantly smaller levels of cyclic guanosine monophosphate (cGMP) and peroxisome proliferator-activated receptor gamma coactivator 1-α (PGC1α) in skeletal muscles after exposure to exercise. Furthermore, in agreement with the previously established musclin ability to interact with NP clearance receptors, but not with NP guanyl cyclase coupled signaling receptors, it was demonstrated that musclin enhances cGMP production in cultured myoblasts only when applied together with ANP. Elimination of the activity-related musclin-dependent boost of ANP/cGMP signaling resulted in significantly lower maximum aerobic capacity, mitochondrial protein content, respiratory complex protein expression and succinate dehydrogenase activity in skeletal muscles. Taken together, these data indicate that musclin enhanced physical endurance by promoting mitochondrial biogenesis.

Introduction

The ability to sustain physical activity is necessary for both quality and longevity of life. Regular exposure to exercise is associated with reduced rates of all-cause mortality. There are multiple mechanisms by which physical activity promotes health, however recently there has been an interest in defining the contribution of circulating proteins secreted by skeletal muscle, termed myokines. Myokines are autocrine, paracrine or endocrine stimuli that may guide local skeletal muscle remodeling, repair, and maintenance or steer systemic adaptation related to physical activity. Understanding the functional role and the signaling pathways of myokines, particularly as they relate to exercise, may reveal new therapeutic targets to promote health and augment the benefits of physical activity.

This study is focused on the recently discovered myokine musclin. Two groups initially identified this peptide: one as bone-derived osteocrin and the second as muscle-secreted musclin. Musclin mRNA expression has been linked to insulin-induced activation of protein kinase B (Akt) that phosphorylates FOXO1, causing it to be exported from the nucleus and thus releasing the musclin encoding gene from transcriptional inhibition. This pathway has been demonstrated to regulate musclin transcription in both cell culture and skeletal muscles. Musclin contains two KKKR (SEQ ID NO: 5) putative serine protease cleavage sites and a region homologous to members of the natriuretic peptide (NP) family. However, musclin does not have two cysteine residues needed to form the a-like structure characteristic for NPs. In line with these structural characteristics it has been demonstrated that musclin binds to the NP clearance receptor, NPRC, with affinity comparable to NPs, but exhibits only weak binding to NPRA and NPRB without activating the linked guanylyl cyclase that is the primary effector of NP physiologic actions. Thus it has been suggested that musclin function may be due to modulation of the action of NPs by competition with them for clearance via NPRC binding. Indeed, musclin overexpression in osteoblast-lineage cells has been shown to result in elongated bones and marked kyphosis, which is similar to the phenotype of mice transgenically overexpressing BNP, CNP, or lacking NPRC. Yet the physiological role of musclin production in skeletal muscles has remained elusive.

In this study, it was demonstrated that musclin production by skeletal muscle is stimulated by physical activity and is paralleled by increased systemic musclin levels. Disruption of normal musclin signaling in mice by knock-out of the musclin encoding gene, Ostn (Ostn-KO), results in diminished exercise tolerance coupled with downgraded activity-related ANP/cGMP/PGC1α-dependent skeletal muscle mitochondrial biogenesis. Thus, this study identifies a physiological role of musclin in enhancing skeletal muscle oxidative capacity and physical endurance.

Results

Musclin Production and Secretion into the Systemic Circulation are Stimulated by Exercise.

Normal skeletal muscle function requires tight coordination with the operation of other organs and systems. Such coordination has been attributed in part to the action of myokines. Specifically, "exercise factors", a subset of myokines whose production and secretion into systemic circulation are stimulated by physical activity, have been shown to modulate skeletal muscle and systemic metabolism, angiogenesis, growth and inflammation.

Figures 1A, 1B, 1C, 1D, 1E:
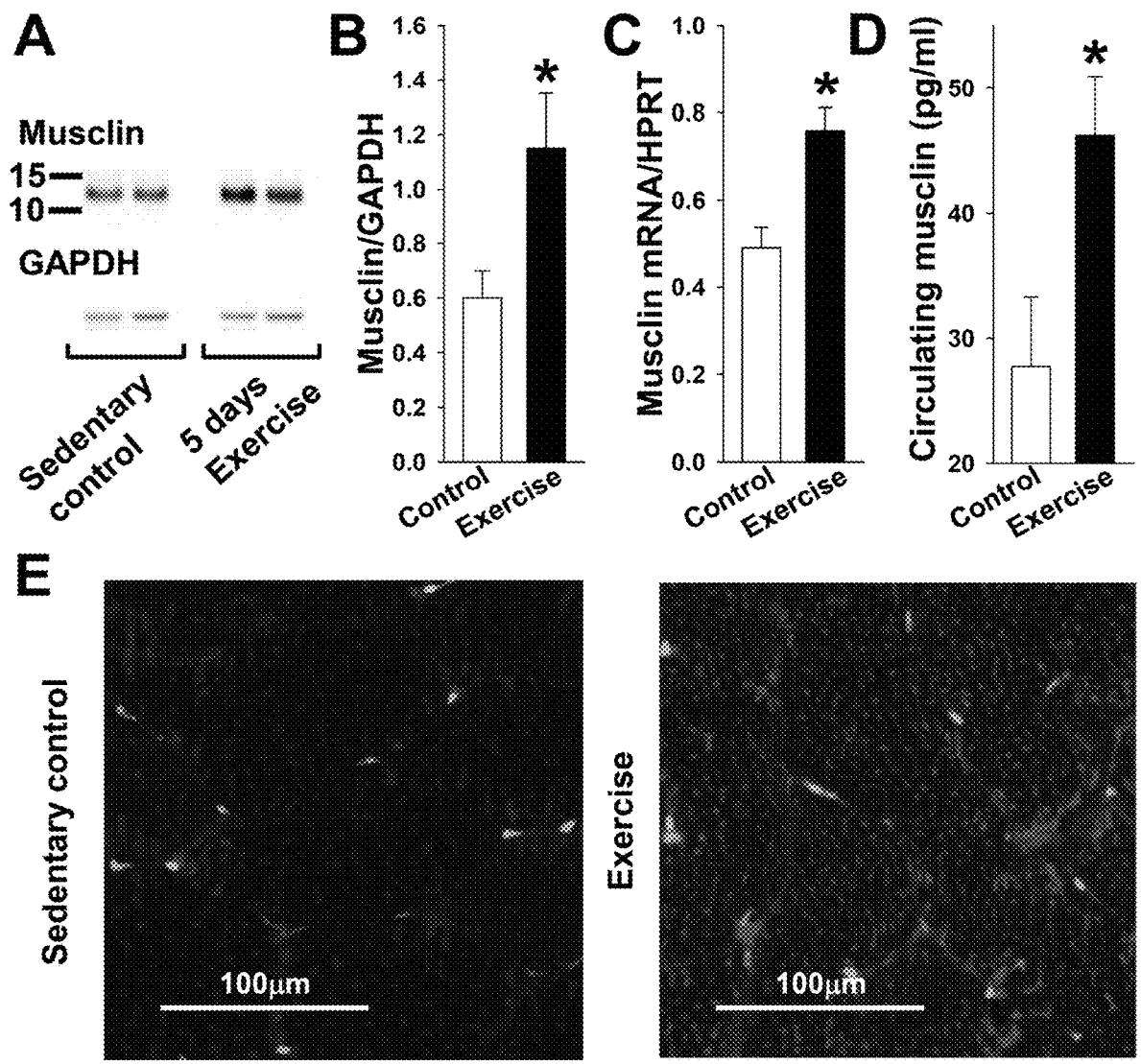
FIGS. 1A-1E. Musclin expression is exercise responsive. Musclin expression was tested in muscles of WT mice after 5 d of treadmill exercise vs. no exercise (control).

To determine whether musclin is an exercise factor, the level of musclin peptide in skeletal muscle was probed in two groups of WT mice: one group that exercised on a moving treadmill for 45 min daily (exercise) and a second group that was placed on the non-moving treadmill for the same amount of time (control). After 5 days of exercise or control treadmill exposure, mice were sacrificed and their tissues harvested by rapid excision and freeze clamp. Proteins were extracted from gastrocnemius muscles and segregated by western blot (FIG. 1A) showing that exercise was associated with a nearly 100% increase in skeletal muscle musclin over control conditions (1.15±0.2 vs. 0.60±0.1 AU, n=5 each, p<0.05, FIG. 1B). A similar increase was demonstrated in skeletal muscle musclin mRNA from tibialis anterior samples (0.75±0.05 vs. 0.49±0.05 AU, n=5 each, p<0.05, FIG. 1C) while musclin mRNA levels in femur were markedly (96-98%) lower and were unresponsive to exercise (0.02±0.002 vs. 0.02±0.003 AU, respectively, n=4 each, p=NS between exercise and sedentary, p<0.05 compared to skeletal muscle mRNA). The increased musclin production by skeletal muscle was paralleled by an increase in the plasma musclin level from 27.71±5.54 pg/ml (n=3) in sedentary control WT mice, to 46.24±4.69 pg/ml in WT mice post-exercise (n=6, p<0.05, FIG. 1D). Furthermore, immunohistochemistry of gastrocnemius cross-sections demonstrated more intense staining for musclin when mice were post-exercise vs. sedentary (FIG. 1E). Thus, musclin production and secretion into the systemic circulation are upregulated in response to exercise, establishing musclin as an exercise factor.

Activity-Induced Musclin Production is Linked to $Ca^{2+}$-Dependent Activation of Akt Regulation of musclin transcription has previously been linked to Akt activation. Akt is a serine/threonine kinase that has emerged as a critical signaling component for the regulation of cellular metabolism, growth, and survival in multiple systems. Akt activity is increased in response to numerous stimuli, including a wide variety of growth factors and hormones activating phosphatidylinositol 3-kinase (PI 3-kinase). Akt can also be activated by mechanisms independent of PI3-kinase, for example in response to increases in intracellular $Ca^{2+}$ or cAMP as occurs with increased muscle contractile activity.

Figures 2A, 2B, 2C, 2D, 2E, 2F, 2G, 2H:
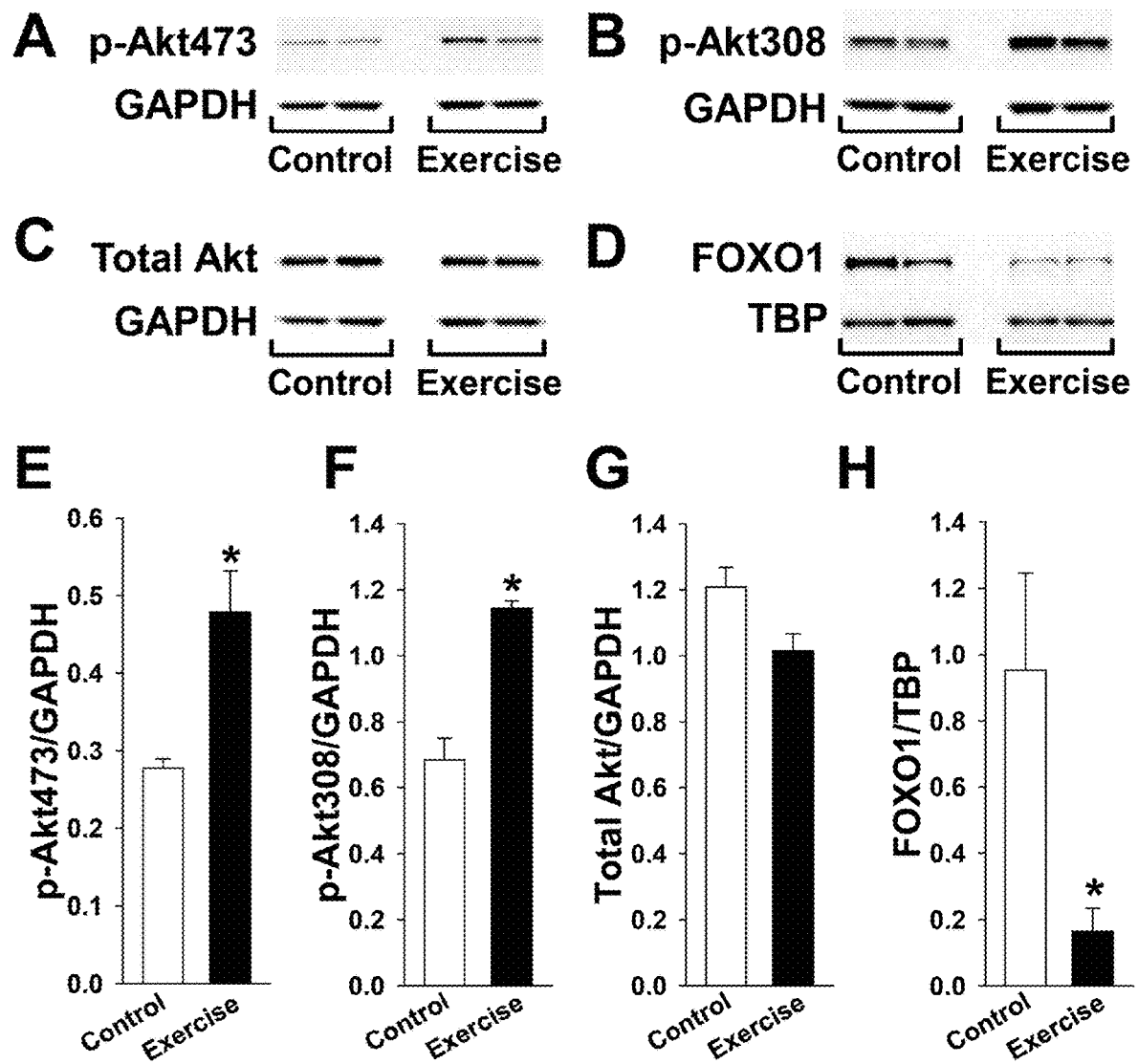
FIGS. 2A-2H. Exercise promotes skeletal muscle Akt phosphorylation and FOXO1 nuclear export. Gastrocnemius of WT mice were assayed after 5 d treadmill exercise vs. no exercise (control). Representative western blots of GAPDH and Akt phosphorylated at FIG. 2A) residue 473, FIG. 2B) residue 308, and FIG. 2C) total Akt in muscle and FIG. 2D) representative western blots of TBP and FOXO1 in nuclear extracts from muscle. Summary statistics for expression of Akt phosphorylated at FIG. 2E) residue 473, FIG. 2F) residue 308, and FIG. 2G) total Akt normalized to GAPDH in muscle and FIG. 2H) FOXO1 normalized to TBP in nuclear extracts from muscle by densitometry of western blots. Akt: protein kinase B, GAPDH: glyceraldehyde 3-phosphate dehydrogenase, TBP: anti-TATA binding protein, FOXO1: forkhead box protein O1. $*p<0.05$ vs. control.

Here it was confirmed that Akt is activated in a model of treadmill-exercised mice. Specifically, the levels of phosphorylated Akt (S473, T308) and total Akt from gastrocnemius of WT mice were compared by western blot (FIG. 2A-C) showing a significant increase in phosphorylated Akt (0.48±0.09 vs. 0.28±0.01 AU, n=5 each, p<0.05 for S473, FIG. 2E, and 1.14±0.02 vs. 0.68±0.07 AU, n=5 each, p<0.05 for T308, FIG. 2F), but not total Akt (1.02±0.05 vs. 1.21±0.06 AU, n=5 each, p=NS, FIG. 2G), in response to exercise vs. sedentary conditions. Akt is a known regulator of FOXO1 nuclear export. Here, it was found that there was a significant increase in phosphorylated FOXO1 (1.473±0.047 vs. 1.185±0.056 AU, n=3 each, p<0.05) but not total FOXO1 (1.380±0.046 vs. 1.337±0.103 AU, n=3 each, p=NS) normalized to GAPDH in gastrocnemius muscle from exercised vs. sedentary muscle (FIGS. 7A-7D). Also, FOXO1 nuclear content quantification by western blot (FIG. 2D) showed a dramatic reduction in response to exercise (0.16±0.07 vs. 0.95±0.29 AU, n=5 each, p<0.05, FIG. 2H). As FOXO1 is known to inhibit musclin encoding gene transcription in skeletal muscle, this exercise-related reduction in nuclear FOXO1 was consistent with the finding of increased musclin mRNA following exercise. Furthermore, it was found that no significant exercise-induced changes occurred in musclin mRNA/HPRT in Akt1-KO mice (0.47±0.10 AU, n=5 vs. 0.45±0.06 AU, n=4, p=NS).

Figures 3A, 3B, 3C, 3D, 3E:
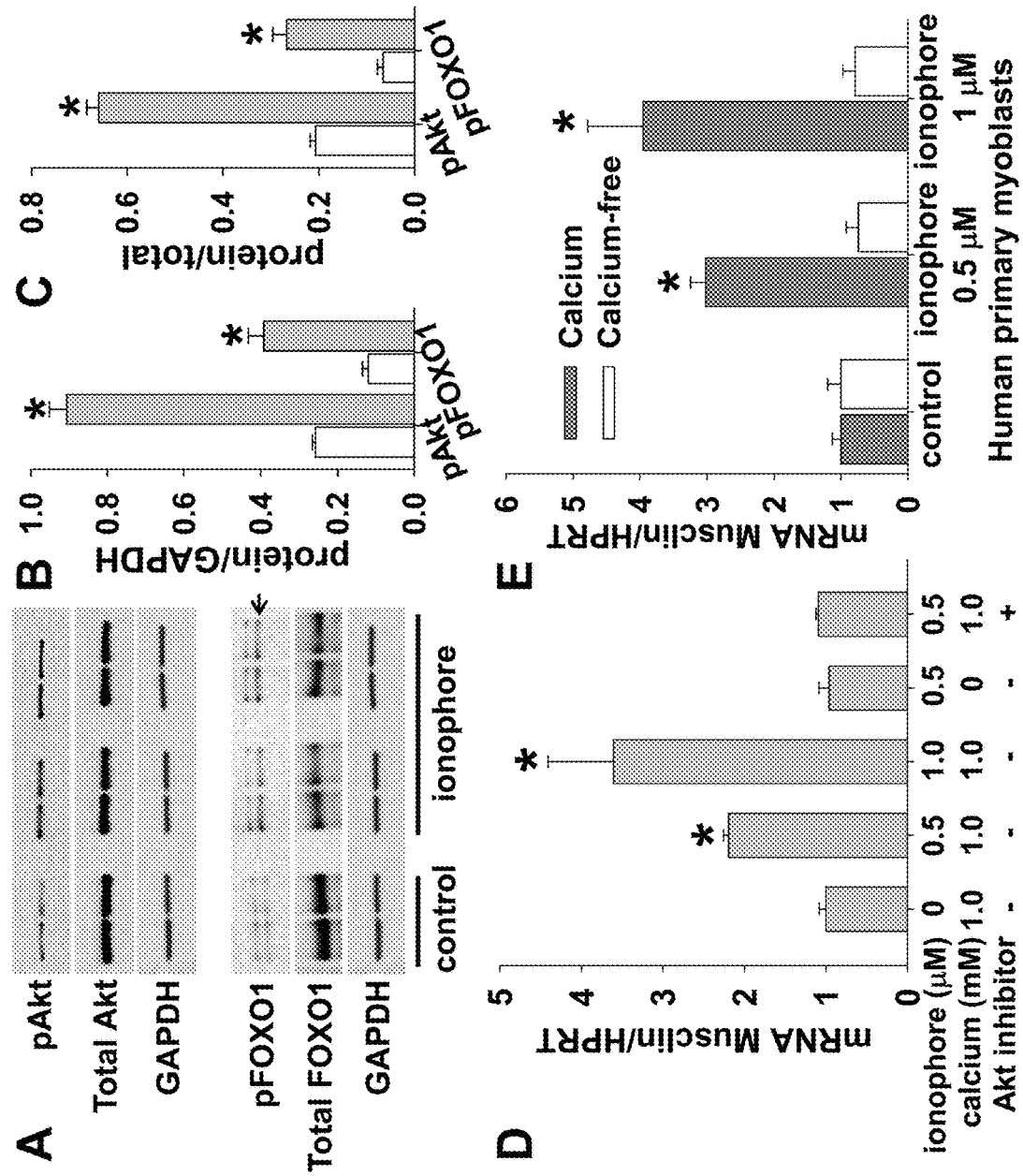
FIGS. 3A-3E. Musclin production is stimulated by $Ca^{2+}$-dependent Akt phosphorylation.

This molecular cascade was verified in a cell culture model of primary skeletal myoblasts isolated from WT mice in which phosphorylation of Akt and FOXO1 were induced by application of a $Ca^{2+}$ ionophore (A23187, Sigma Aldrich, FIG. 3A-C, p-Akt/GAPDH 0.26±0.008, n=2 vs. 0.91±0.05, n=4, pFOXO1/GAPDH 0.12±0.02, n=2 vs. 0.39±0.04, n=4, pAkt/total Akt 0.21±0.01, n=2 vs. 0.66±0.03, n=4, pFOXO1/total FOXO1 0.07±0.01, n=2 vs. 0.27±0.03, n=4, for control and ionophore conditions, respectively, all in the presence of 1 mM $Ca^{2+}$, p<0.05 for all comparisons). This activation of Akt by $Ca^{2+}$ ionophore was paralleled by augmented musclin production (FIG. 3D,E). Specifically, an increase in musclin mRNA was induced by $Ca^{2+}$ ionophore in a dose-dependent manner (1.00±0.08 AU no ionophore vs. 2.20±0.06 AU for 0.5 µM ionophore vs. 3.60±0.81 AU for 1 µM ionophore, all in presence of 1.0 mM $Ca^{2+}$, n=3 each, p<0.05 for each ionophore concentration vs. no ionophore or 'control', FIG. 3D)—a response that was eliminated when myoblasts were pre-treated with Akt inhibitor-viii (Sigma Aldrich, 1.09±0.03 AU, n=3, p=NS vs. control, FIG. 3D), or by removal of extracellular $Ca^{2+}$ from the medium (0.96±0.012 AU, n=3 each, p=NS vs. control, FIG. 3D). The same musclin response to $Ca^{2+}$ was observed in a primary culture of myoblasts isolated from healthy human subjects (ZenBio Inc., Research Triangle Park, NC, 1.0±0.03 AU for no ionophore vs. 3.02±0.23 AU for 0.5 µM ionophore vs. 3.95±0.83 AU for 1 µM ionophore, all in presence of 1.0 mM $Ca^{2+}$, n=3 each, p<0.05 for each ionophore concentration vs. no ionophore or 'control', values in $Ca^{2+}$-free buffer were 1.0±0.05, 0.74±0.18 and 0.79±0.18 AU, respectively, n=3 each, p=NS, FIG. 3E), confirming that this mechanism is not specific to mice. These findings all indicate that exercise-related musclin production is driven by the $Ca^{2+}$-Akt-FOXO1 signaling cascade.

Genetic Disruption of Musclin Production Causes Reduced Physical Endurance

To investigate the physiological significance and function of a physical activity-induced increase in musclin production, a novel mouse model was generated with ubiquitous disruption of the musclin encoding gene, Ostn (genOway, Lyon, FR) and the absence of musclin production in skeletal muscle of Ostn-KO mice vs. WT controls by western blot (FIG. 4A, B) was confirmed. The Ostn-KO mice, housed normally and fed standard chow, exhibit no skeletal deformities or differences in bone density, no growth abnormalities, blood pressure or body composition changes (FIGS. 8A-8D, Table 1) compared to controls at 7-8 weeks of age but do demonstrate lower exercise tolerance than controls.

TABLE 1

Body size, hind-limb bone thickness and length, body composition and basic hemodynamic properties in mice.

|  | Wild-type | N | Ostn-KO | N | p |
|---|---|---|---|---|---|
| Muscle mass GCN (mg) | 84.3 ± 7.0 | 11 | 93.5 ± 6.1 | 12 | .33 |
| Muscle mass QDR (mg) | 97.6 ± 9.7 | 11 | 101.0 ± 7.2 | 12 | .80 |
| Body length (cm) | 9.3 ± .1 | 5 | 9.2 ± .2 | 5 | .41 |
| Fore-limb length (cm) | 2.1 ± .02 | 5 | 2.2 ± .04 | 5 | .61 |
| Hind-limb length (cm) | 2.7 ± .04 | 5 | 2.6 ± .06 | 5 | .80 |
| Systolic BP (mmHg) | 110 ± 2 | 5 | 113 ± 2 | 5 | .33 |
| Diastolic BP (mmHg) | 63 ± 2 | 5 | 61 ± 2 | 5 | .72 |
| Heart rate (beats per min) | 516 ± 10 | 5 | 509 ± 14 | 5 | .66 |
| Hind-limb CT data | | | | | |
| Right femur mean cortical thickness (mm) | .24 ± .02 | 3 | .24 ± .004 | 3 | .75 |
| Left femur mean cortical thickness (mm) | .23 ± .004 | 3 | .23 ± .004 | 3 | 1 |
| Right tibia mean cortical thickness (mm) | .25 ± .007 | 3 | .25 ± .01 | 3 | .87 |
| Left tibia mean cortical thickness (mm) | .25 ± .008 | 2 | .24 ± .003 | 3 | .47 |
| Right femur max cortical thickness (mm) | .30 ± .03 | 3 | .31 ± .003 | 3 | .85 |
| Left femur max cortical thickness (mm) | .30 ± .003 | 3 | .31 ± .01 | 3 | .29 |

TABLE 1-continued

Body size, hind-limb bone thickness and length, body composition and basic hemodynamic properties in mice.

| | Wild-type | N | Ostn-KO | N | p |
|---|---|---|---|---|---|
| Right tibia max cortical thickness (mm) | .37 ± .009 | 3 | .35 ± .02 | 3 | .4 |
| Left tibia max cortical thickness (mm) | .36 ± .03 | 2 | .33 ± .005 | 3 | .35 |
| Right femur length (mm) | 14.46 ± .01 | 3 | 14.13 ± .20 | 3 | .19 |
| Left femur length (mm) | 14.46 ± .05 | 3 | 15.30 ± 1.06 | 3 | .47 |
| Right tibia length (mm) | 17.44 ± .16 | 3 | 17.06 ± .07 | 3 | .10 |
| Left tibia length (mm) | 17.25 ± .15 | 2 | 17.03 ± .07 | 3 | .23 |
| TD-NMR data | | | | | |
| Body weight (g) | 21.2 ± .5 | 15 | 21.9 ± .1 | 26 | .36 |
| Fat (g) | 2.5 ± .1 | 15 | 2.6 ± .1 | 26 | .54 |
| Lean (g) | 16.0 ± .4 | 15 | 16.2 ± .4 | 26 | .74 |
| Fluid (g) | 2.7 ± .1 | 15 | 2.8 ± .1 | 26 | .62 |
| % fat | 11.9 ± .6 | 15 | 12.0 ± .5 | 26 | .88 |
| % lean | 75.5 ± .5 | 15 | 73.9 ± .3 | 26 | .01 |
| % fluid | 13.0 ± .3 | 15 | 12.8 ± .3 | 26 | .67 |

Left lower leg motion artifact prevented tibial measurements in one WT mouse.
KO: knock-out,
CT: computed tomography,
GCN: gastrocnemius muscle,
QDR: quadriceps femoris muscle,
BP: blood pressure.

Specifically, when challenged with a program of treadmill exercise with progressive increase in speed and incline (FIG. 4C), Ostn-KO mice demonstrate a significant deficit in exertional tolerance with respect to duration (71±6 vs. 91±6 min., n=6 each, p<0.05, FIG. 4D), distance (769±102 vs. 1147±121 meters, n=6 each, p<0.05, FIG. 4E) and overall workload (34±5 vs. 53±4 J, n=6 each, p<0.05, FIG. 4F). Similarly, when mice were offered the opportunity for voluntary exercise on running wheels (FIG. 4G), Ostn-KO mice demonstrated significantly lower mean velocity (35±4 vs. 52±4 rotations/5 min., n=6 each, p<0.05, FIG. 4H), duration (303±38 vs. 383±64 min., n=6 each, p<0.05, FIG. 4I) and distance (1505±231 vs. 2218±253 meters, n=6 each, p<0.05, FIG. 4J) during the night when the vast majority of activity was recorded. To confirm that the observed phenotype is related to the absence of musclin in the systemic circulation, mice were implanted with osmotic pumps (Alzet Durect, Cupertino, Calif.) loaded with saline or 50 µg of musclin. This dose resulted in a musclin plasma levels of 69.7±8.8 pg/ml (n=3) comparable with levels observed in mice following exercise as presented in FIG. 1). Voluntary exercise on running wheels (FIG. 4K) was significantly increased in WT mice treated with musclin (n=5) compared to WT mice treated with saline (n=4) with respect to mean velocity (51±7 vs. 16±4 rotations/5 min., p<0.05, FIG. 4L), duration (336±39 vs. 147±10 min., p<0.05, FIG. 4M) and distance (2202±280 vs. 696±179 meters, p<0.05, FIG. 4N). Furthermore, treatment with musclin "rescued" the Ostn-KO mice (n=4) as their exercise activity was equalized to that of musclin treated WT mice (n=5) in terms of night-time mean velocity (53±15 vs. 51±7 rotations/5 min., p=NS, FIG. 4L), duration of running (333±53 vs. 336±39 min., p=NS, FIG. 4M), and distance run (2290±632 vs. 2202±280 meters, p=NS, FIG. 4N). Thus, intact musclin production is critical for optimal exercise performance.

Musclin Boosts Activity-Related cGMP Production in Skeletal Muscle

To address the relationship between exercise, musclin and ANP, WT and Ostn-KO mice were examined following exercise using the same protocol as in FIG. 1 which established a significant exercise-related musclin response in WT mice. A trend was found toward higher plasma ANP levels in exercised WT (n=18 mice in 6 groups) compared to Ostn-KO (n=15 mice in 5 groups) mice, although it did not achieve statistical significance (140.4±19.9 pg/ml vs. 98.2±4.5, p=0.09, FIG. 5A). Furthermore, when gastrocnemius muscles were assayed post-exercise, significantly more cGMP was detected in the muscle of WT compared to Ostn-KO mice (23.13±0.88 fmol/mg vs. 20.62±0.60 skeletal muscle tissue, p<0.05, FIG. 5B). This ANP-musclin interaction with respect to cGMP signaling was further verified in a cell culture model. Specifically, a skeletal myoblast culture exposed to various combinations and concentrations of these two peptides (n=3 each, FIG. 5C) were examined. It was found that, as expected, cGMP production was very low when no peptides were added (0.113±0.003 fmol/µg protein), or when musclin was added without ANP (0.104±0.006 fmol/µg protein for 1 µM musclin and 0.117±0.003 fmol/µg protein for 5 µM musclin, FIG. 5C). Also as expected, exposure to ANP resulted in a vigorous dose-dependent cGMP response (3.491±0.057 fmol/µg protein for 1 µM ANP and 6.046±0.074 fmol/µg protein for 5 µM ANP). Importantly, this response was augmented by the addition of musclin (6.840±0.184 fmol/µg protein for 5 µM ANP+1 µM musclin, p<0.05 vs. ANP 5 µM without musclin, FIG. 5C).

These data support a synergistic relationship between musclin and ANP and are consistent with the hypothesis that competition for $NPR_C$ between musclin and ANP augments local ANP effects due to reduced clearance.

Normal Musclin Signaling Promotes Mitochondrial Biogenesis in Skeletal Muscle

Natriuretic peptide/cGMP signaling is increasingly recognized as a key regulator of metabolic homeostasis, including effects on skeletal muscle mitochondrial biogenesis and oxidative phosphorylation potential. Maximal aerobic capacity ($VO_2$ max) is commonly used to estimate overall aerobic fitness based on cardiopulmonary function and oxidative phosphorylation potential. To determine whether musclin production impacts aerobic capacity as a potential mechanism underlying differences in exercise tolerance, exercise-trained Ostn-KO and WT mice were monitored on a metabolic treadmill equipped for indirect calorimetry (Columbus instruments, Columbus Ohio). After 5 days of training, mice were placed on the stationary treadmill for 30 minutes and then were exposed to the protocol of escalating exercise workload to determine their $VO_2$ max. The resulting oxygen consumption recorded as a function of time reveals a significantly lower $VO_2$ max for Ostn-KO compared with WT (7629±161 vs. 8334±212 ml/kg/hour, n=5 and 4, respectively, p<0.05, FIG. 6A). Interestingly, after 3 weeks of musclin infusion delivered via osmotic pumps (Alzet Durect, Cupertino, Calif.), Ostn-KO and WT mice demonstrated comparable $VO_2$ max (8193±100 vs. 8034±77 ml/kg/hour, n=3 and 4, respectively, p=NS, FIG. 9). These findings suggest musclin signaling may be tied to oxidative phosphorylation through mitochondrial density, size or function. To assess this, electron micrographs of longitudinal sections through tibialis anterior of exercised mice were examined and appear to show smaller mitochondrial size in the Ostn-KO compared to WT mice (FIG. 6B). This corresponds to a significantly lower mitochondrial protein content when normalized to the wet skeletal muscle weight (1.09±0.04 vs. 1.33±0.07 µg/mg tissue, n=6 each, p<0.05, FIG. 6C), and respiratory complex expression (0.24±0.02 vs. 0.31±0.04 AU for CIII and 0.65±0.08 vs. 0.91±0.06 AU for CVI, n=3 each, p<0.05, FIG. 6D, E) in gastrocnemius muscle homogenates, as well as succinate dehydrogenase (SDH) expression as assessed by % of immunohistochemical staining in tibialis anterior cross-sections (43.33±0.65 vs. 49.92±2.09%, n=3 each, p<0.05, FIG. 6F, G) from Ostn-KO vs. WT mice. Furthermore, disruption of normal musclin signaling appears to impact fiber type composition. Specifically, histologic examination of skeletal muscles from Ostn-KO vs. WT mice indicates a shift towards more pure glycolytic type IIb fibers in the KO (FIGS. 10A-10B). Differences between sedentary WT and Ostn-KO mice were less marked (FIGS. 11A-11G), which were consistent with the findings that exercise augments musclin signaling in the WT mice. Specifically, differences in oxygen consumption during treadmill testing (n=4 each), mitochondrial content (0.83±0.20, n=5 vs. 0.71±0.03 µg/mg tissue, n=6, p=NS), and respiratory complex expression normalized to GAPDH in gastrocnemius muscle homogenates (0.64±0.06 vs. 0.60±0.02 for CII, 0.53±0.04 vs. 0.57±0.04 for CIII, 1.35±0.08 vs. 1.36±0.04 for CIV, 0.97±0.07 vs. 0.86±0.03 for CVI, n=4 each, all p=NS) were not significantly different for sedentary WT vs. Ostn-KO mice, respectively, while SDH positive staining of tibialis anterior cross-sections (45.33±0.40 vs. 41.12±1.24%, n=3 each, *p<0.05) exhibited a smaller difference than that in exercise-trained WT vs. Ostn-KO mice. The pattern of distribution of fiber types from muscles of sedentary WT and Ostn-KO was similar to that of their exercise-trained counterparts, consistent with a slower adaptation of fiber type to exercise, except that there was a slightly more prominent component of type IIA fibers in exercised mice (FIG. 12, n=4 each for tibialis anterior and n=3 each for biceps femoris, *p<0.05).

To address the hypothesis that observed differences in skeletal muscle mitochondrial content of Ostn-KO vs. WT mice are driven by cGMP/PGC1α signaling, their tibialis anterior were examined and found that despite similar PGC1α levels at baseline (1.729±0.44 vs. 1.125±0.1 AU, respectively, n=5 and 7, p=NS) an exercise-related increase in PGC1α over this baseline was significantly smaller in Ostn-KO than in WT mice (13.0±0.1% vs. 119.7±29.9% increase respectively, n=3 each, p<0.05, FIG. 5D). In a primary myoblast culture model, induction of cGMP by the combination of musclin and ANP (FIG. 5C) was associated with a significant increase in mRNA of PGC1α (FIG. 5E) and its downstream targets linked to mitochondrial biogenesis, TFAM, NRF1 and NRF2 (FIG. 5F).

These data indicate that exercise tolerance is influenced by musclin via an effect on ANP-dependent PGC1α regulation of skeletal muscle activity-related mitochondrial biogenesis.

Discussion

This study establishes that production of the peptide musclin is upregulated in skeletal muscle in response to physical activity and that musclin is secreted into the systemic circulation. Disruption of musclin signaling in Ostn-KO mice is associated with reduced oxidative phosphorylation potential and exercise tolerance that is corrected by musclin replacement therapy. These findings indicate a previously unrecognized pathway for skeletal muscle metabolic adaptation to exercise.

While forced treadmill exercise was used to demonstrate the responsiveness of musclin production and secretion to exercise, a phenotype was found of decreased endurance and trends toward lower mitochondrial content and higher presence of IIA glycolytic fibers even in untrained Ostn-KO mice compared with WT controls. Importantly, these observed trends and changes in sedentary Ostn-KO become much more obvious and significant after exposure to the treadmill exercise protocol. This indicated that musclin production and secretion, although more easily demonstrated in response to vigorous exercise, are physiologically relevant even for routine daily activities.

The present data support the hypothesis that musclin modulates effects of cardiac NPs due to its ability to interfere with binding to the NP clearance receptor. First it was demonstrated that musclin itself does not induce cGMP production in primary myoblasts but rather potentiates ANP effects. Further, the significance of this signaling was confirmed in vivo. Specifically, it was demonstrated that WT mice have significantly higher muscle levels of cGMP after exposure to exercise compared with Ostn-KO mice. The higher level of muscle cGMP in WT vs. Ostn-KO mice is parallel by a trend toward higher plasma ANP. Elevation of ANP in plasma after physical activity has traditionally been linked to atrial wall stretch, however the present data suggest that increased production of musclin could also contribute to this phenomenon. Of note, it is possible that the measurement here does not reach statistical significance due to significant variability of circulating ANP levels and the inability to use mice as their own controls, as the volume of plasma needed for testing precludes more than a single terminal blood draw per mouse.

An order of magnitude lower production of musclin was detected in the bone of our adult mice compared to that from skeletal muscle. This is consistent with original reports that indicate high musclin expression during early bone development sharply declines in a time- and maturity-dependent manner in both mice and humans. Furthermore, in contrast to skeletal muscle, no exercise-responsive increase in mRNA levels of musclin was observed in bones. Thus, it seems likely that the elevated systemic circulating musclin levels following exercise are largely supported by augmented production and secretion by skeletal muscle.

Identification of the exercise-responsive nature of musclin signaling, along with its systemic circulation, has important implications for our understanding of exercise-dependent NP signaling. Cardiac NPs are increasingly recognized as hormones with a wide spectrum of targets: in addition to traditional targets of vasculature and kidney, recently their effects on skeletal muscle mitochondrial biogenesis, angiogenesis, lipolysis, and adipose tissue remodeling (browning) has been reported. While the current study focuses on one aspect of this signaling network, intramuscular cGMP signaling and mitochondrial biogenesis, it is possible that other cardiac NP signaling targets are similarly affected. For example, musclin may be at least partially responsible for the beneficial effect of exercise on cardiac remodeling. Such targets will be the subject of future investigation.

cGMP signaling has been linked to PGC1α-dependent mitochondrial biogenesis in many studies in different tissues and organs. cGMP production in skeletal muscles is typically linked to nitric oxide signaling, although recently a role for NPs in this process has been established. The present data support the importance NP signaling and its regulation by musclin in cGMP/PGC1α-driven mitochondrial biogenesis. The present data also confirm significantly greater mitochondrial quantity and function by multiple methods and demonstrate the in vivo functional importance by revealing a meaningful increase in the $VO_2$ max, a parameter which reflects many factors including oxidative phosphorylation potential, cardiovascular and pulmonary functions critical for physical endurance, of mice with intact vs. disrupted musclin signaling.

Finally, the present study demonstrated that musclin infusion "rescues" exercise and oxidative capacity in Ostn-KO mice, as well as enhances exercise and oxidative capacity in WT mice, which suggests a potential therapeutic role for musclin. Overexpression of musclin in chondrocytes has been linked to abnormal skeletal growth, but such changes may or may not occur with systemically-delivered musclin.

In summary, this study defines musclin as an exercise-responsive factor promoting skeletal muscle mitochondrial biogenesis and exercise endurance.

Materials and Methods

Ostn-KO Mouse Model

Vector construction and targeted knockout strategy were designed together with genOway (Lyon, France), where mice were generated based on deletion of a 2.1 kb sequence flanking Ostn exon 2 resulting in inactivation of the ATG and signal peptide. Homology sequences were cloned from murine genomic DNA as three independent fragments by polymerase chain reaction (PCR). The first pair of primers (sense: 5'-ATG TTA CAG AAC ATT TGA TCC ATT ACG ACA-3' (SEQ ID NO: 6); antisense: 5'-TGC ACT TCA CAT TAA AAA TTC TTC ACT GC-3' (SEQ ID NO: 7)) amplified the 3341 bp fragment containing the exon 2 upstream sequence. This subclone was used to generate the distal part of the long homology arm of the targeting vector. The second pair of primers (sense: 5'-TAG TAT GCC ATG GTA TTT GTG CTG TGG G-3' (SEQ ID NO: 8); antisense: 5'-TGC TGG TTA CTT TCT CTT CAA GGG CAG-3' (SEQ ID NO: 9)) amplified the 2131 bp fragment containing the exon 2 and neighboring intronic sequences. This subclone was used to generate the proximal part of the long homology arm. The third set of primers (sense: 5'-TTG ATT TGT ACC TAC CTT GGT GCC TGC-3' (SEQ ID NO: 10); antisense: 5'-ACC CAT CAC ATA CAC ACT GCC TTT ACC TAC-3' (SEQ ID NO: 11)) amplified the 2465 bp fragment containing the exon 2 downstream sequence. This subclone was used to generate the short homology arm of the targeting vector and to generate a positive control vector. Amplifications were performed with 15-20 PCR cycles with proof-reading thermostable Taq polymerase (Accuprime Taq DNA polymerase high fidelity, Invitrogen) using genomic C57Bl/6 embryonic stem (ES) cell DNA. Resulting PCR products were subcloned into the pCR4-TOPO vector (Invitrogen) via TA-cloning. Sequencing of the isolated distal long homology arm region resulted in one clone with only a single mutation in the amplified region that was subsequently corrected before vector construction. Sequencing of the isolated proximal long homology arm region and the isolated short homology arm region identified clones without mutation that were used for vector construction. The target vector and a positive control vector were generated with each individual cloning step validated through restriction analysis and partial sequencing. The target vector contained two inserted loxP sites flanking exon 2, the neomycin positive selection gene flanked by flippase recognition target sites and the presence of diphtheria toxin A as a negative selection marker. A robust PCR screening strategy and Southern blot for detection of homologous recombination were designed. The targeting vector was linearized by restriction digest with PmeI. The resulting fragment was isolated, purified, and transfected into ES cells according to standard electroporation procedures. Positive selection was started 48 h after electroporation by addition of 200 µg/ml of G418 (Life Technologies, Inc.). A total of 178 clones were isolated, amplified and screened by PCR to verify homologous recombination at the 3' end of the Ostn locus (sense: 5'-GAA CTT CCT GAC TAG GGG AGG AGT AGA AGG-3' (SEQ ID NO: 12); antisense: 5'-CTC TTC TCT GGC TGT GGG TGG AGA C-3' (SEQ ID NO: 13)) with the expected amplified product size of 2159 bp. Eighteen clones recombined at the 3' end of the Ostn locus were analyzed by a second PCR to test for insertion of the distal loxP site at the 5' end of the locus. Of the 18 tested ES cell clones, 3 were positive for the presence of the distal loxP site. These 3 recombined clones were further verified by Southern blot analysis. Recombined ES cells were injected into albino C57Bl/6 blastocysts, giving rise to two highly chimeric males (>50%) identified by coat color markers. These male mice were bred with C57Bl/6 Cre recombinase expressing deleter mice to excise the loxP-flanked sequence and generate heterozygous mice carrying the constitutive knock-out allele. Genotyping by PCR of pups derived from F1 breeding allowed identification of a pup with complete heterozygous Cre-mediated excision of Ostn. A second breeding of this male with C57Bl/6 wild-type females allowed the generation of additional heterozygous mice with complete Cre-mediated excision of Ostn. Knock-out and wild-type alleles were further verified by Southern blot in these animals. Ostn mice were used to generate $Ostn^{-/-}$ (Ostn-KO) and wild-type (WT) controls through further breeding cycles.

Genotyping:

Genotyping was performed on tail tip DNA extracted with the Dneasy Blood and Tissue Kit (Qiagen). PCR was performed using Platinum Blue PCR Supermix (Invitrogen). To detect the amplification product of the knock-out allele of 2395 bp and the WT allele of 4420 bp, the following primers were used: Forward: 5'-GTG AGG TTA TGA ACA TTC CAA CAG CTA TAT CC-3' (SEQ ID NO: 14) and Reverse: 5'-ATG GGG TTA TTT TCC TTG TCC ACC TAC C-3' (SEQ ID NO: 15).

Akt1-KO Mouse Model

Akt1-KO mouse were purchased from Jackson Laboratory (Bar Harbor, Me.).

Animal Experiments

All animal protocols conform to the Guide for the Care and Use of Laboratory Animals generated by the Institute for Laboratory Animal Research, National Research Council of the National Academies. All protocols were approved by the University of Iowa Institutional Animal Care and Use Committee. Ostn-KO and littermate C57Bl/6 WT control mice or Akt1-KO (Jackson Laboratory, Bar Harbor, Me.), 7-8 weeks old, of either gender, were used for all experiments. For all experiments, mice were anesthetized with inhaled isoflurane (5% induction, 1-1.5% maintenance, Piramal Healthcare, Andhra Pradesh, India) to maintain a respiratory rate of approximately 50-60 breaths per minute.

Skeletal Reconstruction:

Micro-computed tomography (CT) images of the mice were acquired with the Siemen's Inveon PET/CT scanner. CT parameters for acquisition were; voltage of 80 kV and tube current of 500 µA, 220 rotation degrees with 360 steps, medium resolution magnification and a binning of 2. Projections were reconstructed into images using the manufacturer's software with a downsample factor of 1, beam hardening correction, bilinear interpolation, and Shepp-Logan reconstruction filter (ultimate image pixel size of 36.15 micrometers). Images were analysis using ImageJ (version 1.50b) with the BoneJ (version 1.3.12) plugin. Femurs and tibia were cropped and rotated to measure length. Only cortical bone was measured for thickness. For femurs, a 0.54 mm section of bone was measured 3.6 mm from femoral distal growth plate. For tibias, a 0.54 mm section of bone was measured 3.6 mm from the tibial proximal growth plate. The sections were converted to binary images automatically using the BoneJ plugin, and then measured for thickness with the plugin's Thickness tool. 3D images were created using the Inveon Research Workplace (version 4.2) multimodal 3D visualization software.

Physical Characteristics:

Calipers were used to measure limb lengths from hip or shoulder joint to the tips of the digits in the fully extended limbs, and body length from nose tip to anus, of anesthetized mice. Blood pressure was measured by tail cuff method in restrained, awake mice acclimated to the apparatus (Vis-iTech BP Systems).

Body Composition:

Whole body composition was obtained by time-domain nuclear magnetic resonance under isoflurane anesthesia (Bruker Minispec; Billerica, Mass.). Osmotic pumps: Osmotic pumps (model 1004, 100 µl volume, 0.11 µl/hr release rate, 28 days duration, Alzet Durect, Cupertino, Calif.), loaded with saline vs. 50 µg of mouse musclin peptide (SFSGFGSPLDRLSAG SVEHRGKQRKAVDHS-KKR (SEQ ID NO: 4), corresponding to amino acids 80-112, Gen Bank ID: AAS87598.1, synthesized by Biosynthesis, Lewisville, Tex.) were surgically implanted within the peritoneal cavity of mice under sterile conditions and general anesthesia. Mice recovered for 7 days before exercise testing was performed.

Exercise Protocols:

A multi-lane treadmill (Columbus Instruments, Columbus, Ohio) was used to simultaneously exercise model mice with their controls. Mice were acclimated on the treadmill daily for 3 days for 20 min/day a velocity of 3.5 m/min and 15° inclination. After this acclimation period mice were exercised daily for 5 consecutive days at a speed of 12 m/min and inclination of 15° for 45 min/day except for the final day when mice were exercised for 20 min immediately before sample (blood, tissue) collection. To test exercise endurance, the exercise protocol consisted of stepwise increases in either incline or velocity at 3 min intervals until mice were no longer able to match the treadmill speed. For indirect calorimetry, oxygen consumption ($VO_2$) and $CO_2$ generation were measured using a two-lane modular treadmill connected to the Oxymax indirect calorimetry system (Columbus Instruments, Inc.). The calorimeter was calibrated before each measurement with a standard span gas (0.501% $CO_2$, 20.53% $O_2$ balanced with $N_2$), and cross-calibrated against room air before each experiment.

Voluntary Performance on Running Wheels:

Mice were housed in individual cages with free access to attached running wheels (Columbus Instruments, Columbus, Ohio). Running distance was calculated as $1/6\pi D \cdot \Sigma RMP_i$, where D is wheel diameter and $\Sigma RMP_i$ is sum of averaged RPM values.

Blood Collection:

Terminal blood collection was performed by direct cardiac puncture.

Molecular Biology

RNA isolation and quantitative reverse transcriptase polymerase chain reaction (qRT-PCR): Total RNA from mouse tissues and primary myocytes was isolated using RNeasy RNA Isolation Kit (Qiagen). A 1 µg primary myocyte or tissue RNA sample was used to synthesize cDNA in 50 µl reactions using Oligo(dT) as primer and SuperScript III Reverse Transcriptase (Invitrogen). Quantitative real-time PCR was performed on Mastercycler epgradient S (Eppendorf) using SYBR green based PCR reactions. For quantitative RT-PCR, 1 µl of reverse transcription reaction was mixed with 10 pmoles each specific primer and 12.5 µl SYBR PCR Master Mix (BioRad). The reaction was incubated for 40 cycles consisting of denaturation at 95° C. for 10 s and annealing/extension at 59.9° C.—for musclin, HPRT, Nrf2, 56° C.—for PGC1α, Tfam, Nrf1, for 1 min. The quality of the PCR product was routinely checked by a thermal denaturation curve following the qPCR reactions. The threshold cycle (CT) was determined by Realplex2 software (Eppendorf), and quantification of relative mRNA levels was performed by relative mRNA levels was performed by $\Delta\Delta CT$ method. The primers used in this study are HPRT: HPRTF—GGA CCT CTC GAA GTG TTG GAT AC (SEQ ID NO: 16), HPRTR—GCT CAT CTT AGG CTT TGT ATT TGG CT (SEQ ID NO: 17); musclin: MuscF-TGT GGA CTT AGC ATC ACA GG (SEQ ID NO: 18), MuscR-AGC TGA GAG TCT GTC AAG G (SEQ ID NO: 19); PGC1α: PGC1aF-TGA TGT GAA TGA CTT GGA TAC AGA CA (SEQ ID NO: 20), PGC1αR-GCT CAT TGT TGT ACT GGT TGG ATA TG (SEQ ID NO: 21); TfamF—GGA ATG TGG AGC GTG CTA AAA (SEQ ID NO: 22), TfamR—TGC TGG AAA AAC ACT TCG GAA TA (SEQ ID NO: 23); Nrf1F—CGC AGC ACC TTT GGA GAA (SEQ ID NO: 24, Nrf1R—CCC GAC CTG TGG AAT ACT TG (SEQ ID NO: 25); Nrf2F—CAG CTC AAG GGC ACA GTG C (SEQ ID NO: 26), Nrf2R—GTG GCC AAA GTC TTG CTC C (SEQ ID NO: 27).

Western blotting: Whole cell protein extracts were prepared by homogenizing skeletal muscle tissue in NaCl 150 mM, Tris-HCl 50 mM (pH 7.8), supplemented with 1.5% Triton X-100, protease and phosphatase inhibitors (Roche). Nuclear extracts were obtained using the Subcellular Protein Fractionation Kit for Tissues (Thermo Scientific).

Electrophoresis was performed on 3-8% gradient Nu-Page Tris-Acetate or 10% Nu-Page Bis-Tris gels and transferred to 0.2 µm Sequi-Blot PVDF membranes (Bio-Rad). The membranes were blotted with total AKT1 and phospho-AKT1(S437, T308, Cell Signaling), FOXO1 (Cell Signaling), total OXPHOS (rodent, Abcam), musclin (custom rabbit IgG produced against partial mouse musclin sequence NH2-sfsgfgspldrlsagsvehrgkqrkavdhskkr-COOH (SEQ ID NO: 4), corresponding to amino acids 80-112, Gen Bank ID: AAS87598.1, Anaspec, Fremont, Calif.), and GAPDH (Santa Cruz Biotechnologies) antibodies. Densitometric analysis of western blots was performed using Adobe Photoshop (Adobe Systems, San Jose, Calif.).

Enzyme-Linked Immunosorbent Assays:

96-well ELISA Maxisorp plates (Nunc) were coated with custom rabbit anti-musclin IgG (Anaspec) at 1 µg/well in BupH carbonate-bicarbonate buffer, pH 9.4 (Thermo Scientific) at 4° C. overnight. On the next day plates were washed with TBS/0.05% Tween 20 and blocked with 5% BSA/TBS for 1 hr at room temperature. Synthetic musclin peptide was used as a standard (NH2-sfsgfgspldrlsagsvehrgkqrkavdhs-kkr-COOH (SEQ ID NO: 28), corresponding to amino acids 80-112, Gen Bank ID: AAS87598.1, synthesized by Biosynthesis, Lewisville, Tex.). EDTA-plasma samples and diluted standards were applied to the ELISA plates and incubated overnight at 4° C. Plates were washed and incubated with biotinylated rat monoclonal anti-musclin IgG (clone #311417, R&D Systems) for 1.5 hr at room temperature. Plates were washed and incubated with SA-HRP conjugate 1 hr at room temperature, then washed and incubated with the QuantaBlu Fluorogenic Peroxidase Substrate (Thermo Scientific). Fluorescence was detected at 325/420 nm.

Cyclic GMP levels were measured using cyclicGMP EIA kit (Cayman Chemical Company, Ann Arbor, Mich.). Mice were exercised for 5 days, 12 m/min, 45 min before tissue collection. At the day of the experiment mice were exercised 12 m/min, 20 min, sedated with isoflurane and gastrocnemius muscle tissue was collected. Cyclic nucleotides were extracted using 5% trichloracetic acid. Samples were acetylated and used for cGMP level measurements according to the manufacturer's protocol.

ANP levels in plasma were measured using ANP (Rat, Mouse) Fluorescent EIA Kit Ultra-Sensitive (Phoenix Pharmaceuticals). Plasma samples from three mice were combined to collect 1 ml of EDTA-plasma for ANP extraction.

Mitochondrial Content:

Mitochondrial protein fraction was isolated from gastrocnemius muscle using Mitochochondria Isolation Kit (Thermo Scientific) according to manufacturer's protocol. Mitochondria protein content was determined as amount of mitochondrial protein per mg of wet tissue.

Cell Culture:

Mouse primary myoblasts were isolated from gastrocnemius muscle of 4-6 weeks old mice. Fresh muscle tissue was digested with 2 mg/ml collagenase II in DMEM-F12 for 1.5 h at 37° C.; then 30 min at 37° C. with 1 mg/ml collagenase II and 0.5 mg/ml dispase in DMEM-F12. Tissue was ground and passed through a 100 µm then 70 µm cell strainer and spun at 1000 rpm for 10 min. Myoblasts were resuspended in DMEM-F12 supplemented with 20% FBS, 40 ng/ml bFGF, non-essential amino acids, 1 mM β-mercaptoethanol. Cells were plated on matrigel coated dishes. Cells were maintained in DMEM-F12 supplemented with 20% FBS, 10 ng/ml bFGF, non-essential amino acids, 1 mM β-mercaptoethanol until 80% confluent. Then they were differentiated in DMEM-F12 supplemented with 2% FBS and insulin-transferrin-selenium for 10 days. Human skeletal myoblast primary culture (lot #SLSK002, Zenbio, Research Triangle Park, NC) was maintained according to the supplier's manual.

Histology

Muscles were dissected from anesthetized mice, embedded in OCT compound and frozen in 2-methylbutane pre-cooled at −165° C. in liquid nitrogen. Muscles were stored at −80° C. until used. For histology, 10 µm cross sections, cut using a Microm cryostat, cooled to −20° C., were mounted on positively charged slides (Superfrost/Plus, Fisher Scientific, USA) and stored at −80° C. until used.

Fiber Type Composition:

Serial cross sections were labelled simultaneously with anti-MHC primary I, IIA, IIB or IIX antibodies (BA-F8 anti-MHC-I mouse IgG2b, SC-71 anti-MHC IIA mouse IgG, 6H1 anti-MHC IIX mouse IgM, and FB-F3 anti-MHC IIB mouse IgM, University of Iowa Developmental Studies Hybridoma Bank). Slides were then incubated with secondary antibodies (Alexa 647 anti-mouse IgG2b, Alexa 488 anti-mouse anti-IgG and Alexa 568 anti-mouse IgM, Life Technologies). Slides were stored at −80° C. until imaged. Control sections were also stained without the primary antibody to test for non-specific secondary antibody binding. Images were obtained by confocal microscopy (LSM 510 Meta, Carl Zeiss).

Succinate Dehydrogenase (SDH) Staining:

Frozen tissue sections were incubated in buffer (50 mM sodium succinate, 50 mM sodium phosphate and 0.5 mg/ml nitro blue tetrazolium) for 60 min at 37° C., followed by washes with $H_2O$ then 30%, 60% and 90% acetone solutions to remove unbound nitro blue tetrazolium, and dehydration with sequential 70%, 80%, 90% and 100% EtOH and 100% xylene washes before mounting and imaging by light microscopy (BX-51, Olympus).

Musclin Staining:

Tissue cross sections were labelled with anti-musclin primary antibody (Santa Cruz), then incubated with anti-rabbit Alexa 568 antibody (Life Technologies). Nuclei were stained with SYSTO 16 green fluorescent nucleic acid stain (Life Technologies). Images were obtained by confocal microscopy (LSM 510 Meta, Carl Zeiss).

Transmission Electron Microscopy

Muscles were fixed in 2.5% gluteraldehyde and 0.1 M $Na^+$ cacodylate buffer, pH 7.2, overnight at 4° C., followed by three 20-min washes in the same, fixed in 4% $OsO_4$, washed in 0.1 M sodium cacodylate buffer, then $dH_2O$, followed by 2.5% uranyl acetate. A series of ethanol washes was used to dehydrate the sample, which was then exchanged with an ethanol and Spurr's mixture series of increasing Spurr's concentration, culminating in a final solution of 100% Spurr's resin. Muscles were embedded in Spurr's resin at 60° C. for 24-48 h. Ultramicrotomy was carried out at 90 nm and samples collected on 200 mesh formvard grids for staining with uranyl and lead. Stained sections were examined with a JEOL JEM-1230 transmission electron microscope and digital images were collected with a Gatan UltraScan 1000 2k×2k CCD camera.

Statistics

Results are expressed as mean±SEM. Comparisons between two groups were made using the 2-sided Student's t-test and between more than two groups using analysis of variance (ANOVA). A p value <0.05 was considered statistically significant. Sigma Plot 11 was used for all statistical analyses.

Example 2

Musclin Promotes Exercise Endurance and Recovery from Catabolic Stress Through Pathways that Stimulate Net Protein Synthesis and Promotes Resistance to Workload-Induced Apoptosis Through Upregulation of OPA1

Physical activity initiates a broad spectrum of cellular and molecular adaptations including highly coordinated activation of autophagy and mRNA translation pathways that enable physical performance at an enhanced intensity or duration. One of the vital regulators of these processes is mTOR, contained within the multi-protein complexes 1 or 2 (mTORC1 or 2) which integrate inputs from major intracellular and extracellular signals. When energy substrates and growth factors are available, mTORC1 activation stimulates synthesis and inhibits degradation of protein. Among effectors of mTORC1 signaling on protein synthesis, the two best established groups are the eukaryotic translation initiation factor 4E-binding proteins (4EBPs) and ribosomal protein S6 kinases (S6Ks). Their phosphorylation by mTORC1 facilitates recruitment of mRNA to the ribosome and increases translation initiation rates of multiple protein encoding genes underlying skeletal muscle remodeling. At the same time, mTORC1-driven phosphorylation of an inhibitory site on unc-51 like autophagy activating kinase 1 (ULK1) limits autophagy.

We propose that musclin/ANP signaling triggers mTORC1 activation to suppress autophagy and enhance protein synthesis.

While exercise is one of the most effective ways to promote overall and skeletal muscle health and well-being, prolonged or high-intensity physical activity can cause skeletal muscle damage, with eccentric activity being more damaging than isometric activity. Untrained muscles are particularly susceptible to such damage. Initially, inflammatory and necrotic processes were considered as the predominant mechanism for such damage, but more recently a role for apoptosis has been identified. Apoptosis in skeletal muscle displays the unique feature of loss individual myonuclei with their relative portion of sarcoplasm resulting in fiber atrophy rather than death. Better understanding of the molecular mechanisms underlying muscle loss driven by apoptosis will help not only to optimize physical training and rehabilitation, but also development of therapies for muscle pathologies linked to apoptosis such as statin-induced myopathy, sympathetic overstimulation and chronic limb ischemia.

Potential mechanisms promoting skeletal muscle apoposis have been connected to disturbances in mitochondrial homeostasis and release of pro-apoptotic factors such as cytochrome C. A key regulator of mitochondrial homeostasis is OPA1, a dynamin-related large GTPase located on the inner membrane of mitochondria at the narrow junctions between cristae and the boundary membrane. A primary function of OPA1 is participation in fusion of the inner mitochondrial membranes and promotion of mitochondrial networking. However, it is also involved in functions such as mtDNA stability, maintenance of mitochondrial respiratory complex expression and protection against apoptosis through mitochondrial cristae remodelling that acts to prevent release of cytochrome C and ROS. Mild transgenic overexpression of OPA1 protects mice from muscle atrophy. Thus we propose the use of musclin to promote OPA1 expression and resistance to skeletal muscle apoptosis.

Skeletal muscles are the largest bodily protein reservoir and serve as a source of amino acids that can be used for energy production by various vital organs and for maintenance of normoglycemia in response to catabolic states, such as starvation, cancer, sepsis, burn injury, heart failure, infection and immobility. However, excessive and sustained protein degradation along with reduced protein synthesis may result in skeletal muscle wasting which is associated with increased mortality. Muscle catabolism during critical illness involves aspects related to specific diseases, such as inflammation, hypoxemia, and activation of catabolic hormones (e.g., cortisol and catecholamines), as well as "universal" factors associated with any severe illness, such as immobility and limited or absent nutrition. Both musclin production by skeletal muscles, and ANP from the heart, have been recognized as responsive to nutritional status: suppressed under starvation and upregulated by refeeding, thus we propose to use musclin during recovery from catabolic stress to boost skeletal muscle cGMP signaling and activate mTORC1 to support an anabolic shift in the autophagy/protein synthesis balance during recovery from catabolic stress.

Results

All results are expressed as mean±S.E. Mice with ubiquitous disruption of the musclin encoding gene (Ostn-KO) exhibit no musclin secretion and reduced exercise tolerance, decreased $VO_{2max}$, inferior skeletal muscle mitochondrial content and reduced levels of the master regulator of mitochondrial biogenesis, PGC1α, after exercise training. These findings are paralleled by more pure glycolytic fibers and greater fatigability in tibialis anterior (TA) muscles of exercise-trained Ostn-KO vs. WT mice (FIGS. 13A-13C). We previously showed reduced skeletal muscle production of cGMP immediately following exercise in Ostn-KO vs. WT mice and a synergistic effect of musclin with ANP on cGMP production in myotube culture. To further verify the physiologic relevance of this musclin-dependent cGMP production, we measured phosphorylation of GSK3β at residue S9, a known target for PKGI, and found significantly less of the phosphorylated form in the skeletal muscles of Ostn-KO than WT 1 h after last treadmill exercise (FIGS. 14A-14B).

GSK3β phosphorylation is associated with increased autophosphorylation of mTOR at S2481 (FIGS. 14A-14B). Furthermore, consistent with the known activating effect of GSK3β inhibition on mTORC1, we find increased phosphorylation of the mTOR targets 4EBP1, P70S6K and ULK1 in skeletal muscles of trained WT vs. Ostn-KO mice 1 h after last exercise (FIGS. 15A-15B). Phosphorylation of GSK3β, mTOR and mTOR targets was not significantly different in untrained Ostn-KO and WT mice (data not shown). In agreement with the established effect of mTOR on protein synthesis, we find significantly reduced overall skeletal muscle protein synthesis in trained Ostn-KO vs. WT mice, assessed by surface sensing of translation (SUnSET) 60 min after the last treadmill session (FIGS. 16A-16G). We also find that skeletal muscle autophagy flux 1 h after last exercise is increased in exercise-trained Ostn-KO vs. WT, as reflected in higher LC3A II/I ratio and lower expression of P62 on western blots (FIGS. 16A-16G). To further establish the effect of musclin on mTOR activity, WT mice were implanted with osmotic pumps delivering musclin (1 ng/g/h i.p.) or normal saline (0.1 μl/h i.p.) for 7 d with musclin infusion inducing a plasma level comparable with that observed after exercise training. Western blot of protein from skeletal muscles of musclin-, vs. saline-treated mice showed greater phosphorylation of mTORC1 targets (FIG. 17). Taken together, these data suggest that musclin promotes skeletal muscle cGMP production in response to exercise with consequent activation of mTORC1 and an anabolic shift in the autophagy/protein synthesis balance that supports fatigue resistance.

An important feature of skeletal muscle is its ability to adapt to the types and intensity of physical demands by adjusting fiber type, energetics and structure, among others. This plasticity or "trainability" is critical for optimal skeletal muscle performance. We recently demonstrated that normal musclin signaling is important for exercise-induced upregulation of PGC1α, mitochondrial mass, and myofiber remodeling in response to exercise (FIGS. 14A-14B). Furthermore, our preliminary results indicate that disruption of activity-induced musclin signaling also results in significantly reduced mTORC1 activation and protein synthesis paralleled by greater fatigability (FIGS. 13A-13C, 14A-14B, 15A-15B, 16A-16G, 17A-17B). Based on these data, and the established ability of mTORC1 to enhance not only overall protein translation initiation but specifically translation of PGC1α. Thus we propose musclin-ANP-cGMP-PKGI-GSK3β-mTORC1 cascade drives musclin-dependent modulation of the autophagy/protein synthesis balance and specifically mitochondrial biogenesis critical for fatigue resistance and enhanced physical performance.

Figures 18A, 18B, 18C, 18D:
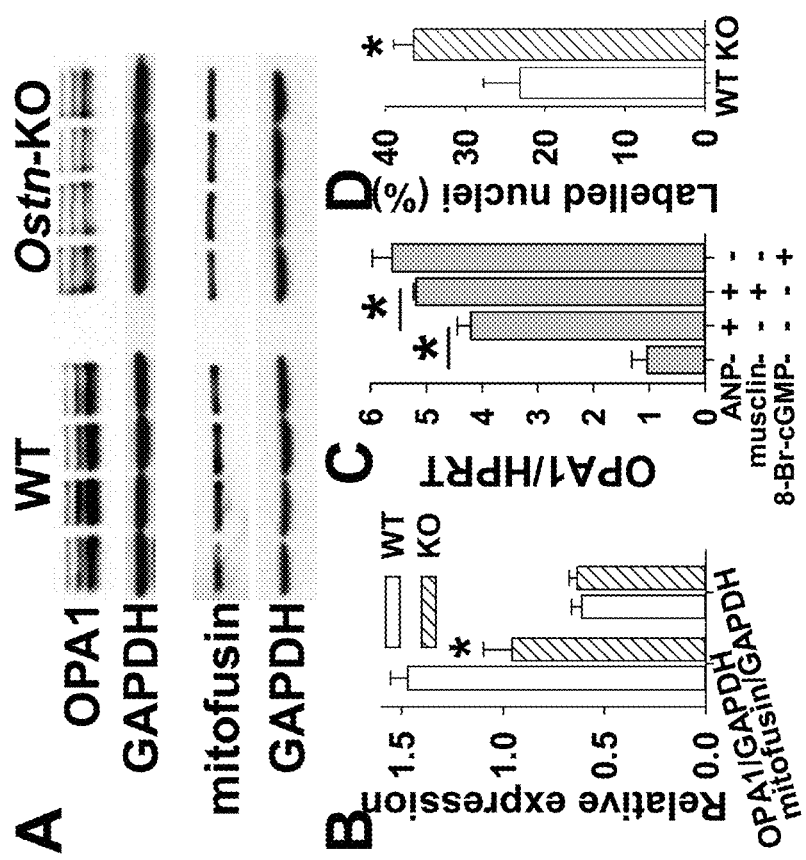

Our preliminary data indicate that after exercise training skeletal muscle expression of OPA1 is reduced in Ostn-KO vs. WT (FIGS. 18A, 18B) despite similar OPA1 in untrained mice (0.79±0.19 vs. 1.02±0.14, n=4 each, respectively, p=NS). OPA1 mRNA expression is confirmed to be responsive to the synergistic effect of musclin and ANP in myotube culture (FIG. 18C). In trained Ostn-KO vs. WT mice we also find that downhill (eccentric) running results in increased markers of myofiber apoptosis (FIG. 18D).

Figures 19A, 19B, 19C, 19D, 19E:
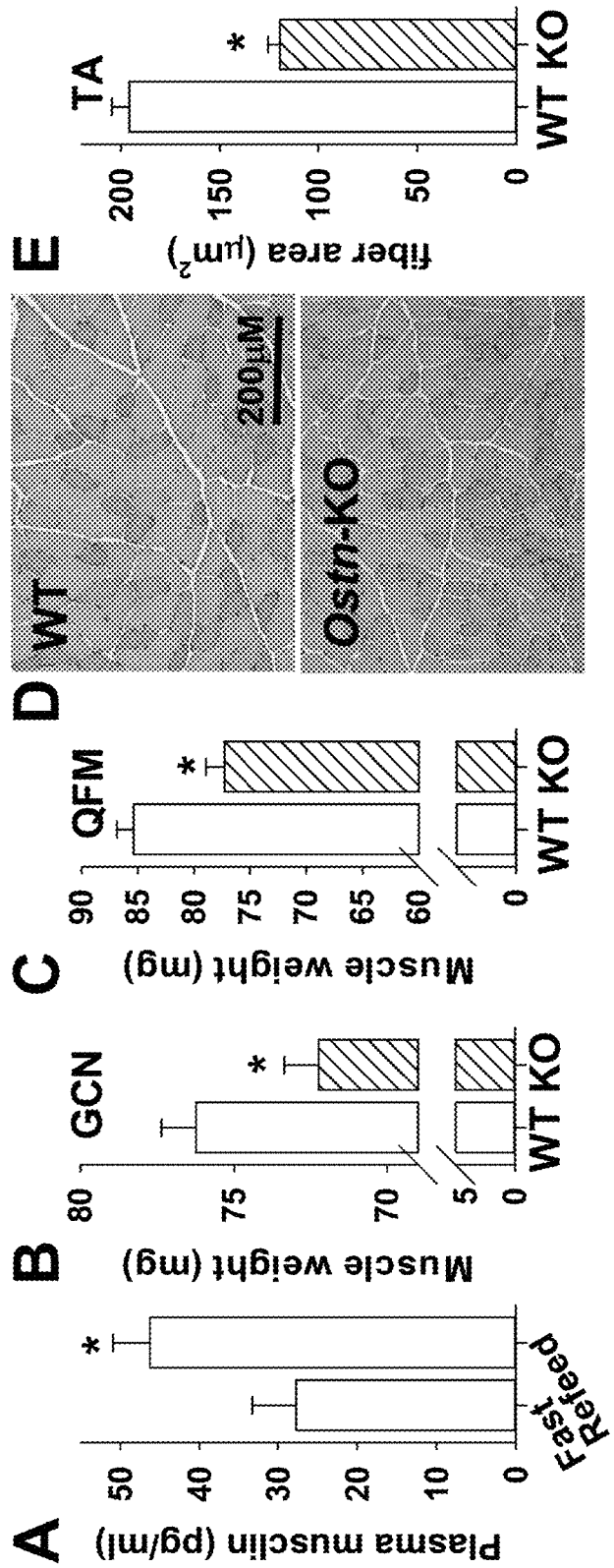
Figures 20A, 20B:
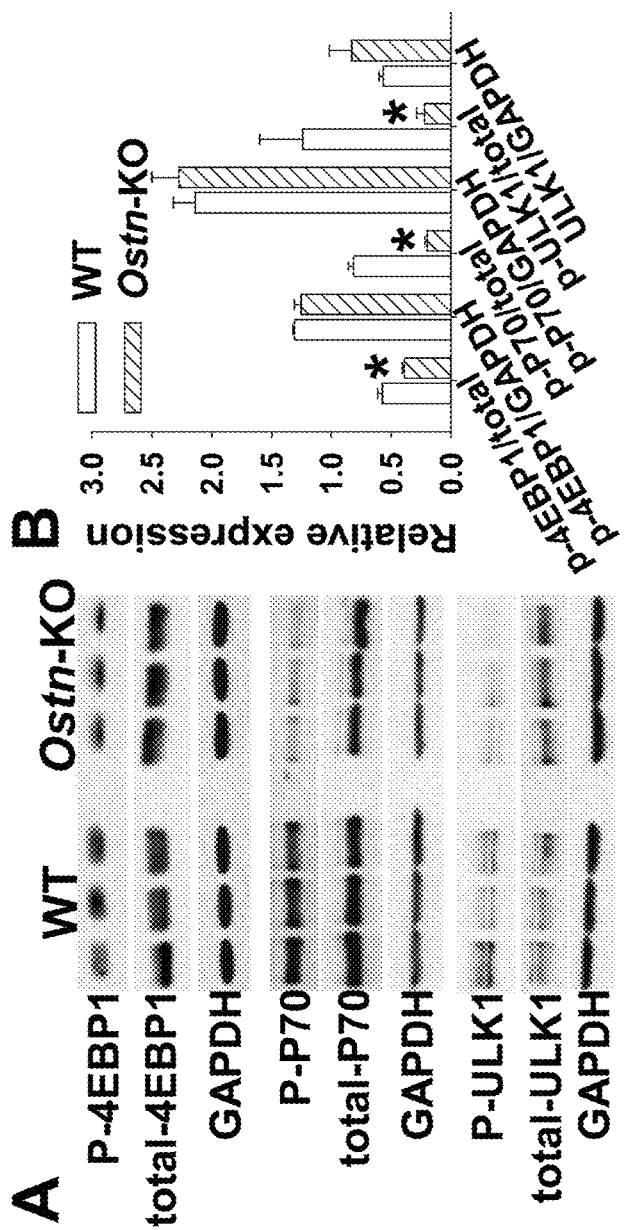

In WT mice fasted for 48 h, plasma musclin is increased when tested 1 hour after refeeding (FIG. 19A). While muscle weight and fiber area are not significantly different at baseline between WT and Ostn-KO, we find that intact musclin signaling in WT vs. Ostn-KO mice is associated with significantly improved muscle weight and fiber area when tested 4 h after fasting/refeeding (FIGS. 19A-19E) despite similar body weight at baseline (24.23±0.30 vs. 23.70±0.52 g) and 4 h after refeeding (21.12±0.34 vs. 21.04±0.47 g), blood glucose at 48 h fast (54.0±2.2 vs. 49.2±1.7 mg/dL) and 4 h refeeding (269±22.7 vs. 317±28.9 mg/dL) respectively (n=5 each, all p=NS). Food intake at 4 h post-fast (1.6±0.2 vs. 2.0±0.5 g, n=3 each, p=NS) and insulin level at 4 h refeeding were also similar (1.16±0.23, n=6 vs. 1.47±0.24 ng/mL, n=7, p=NS). Elevated plasma musclin is paralleled by increased phosphorylated GSK3β in WT vs. Ostn-KO GCN 1 h after refeeding (0.89±0.07 vs. 0.68±0.01 p-GSK3β/total, n=4 each, p<0.05), although no differences in total GSK3β content are identified (1.41±0.09 vs. 1.44±0.07 total GSK3β/GAPDH, n=4 each, p=NS). The mTOR targets 4EBP, P70S6K, and ULK1 S757 show significantly less phosphorylation 1 h after refeeding in Ostn-KO vs. WT mice (FIGS. 20A-20B).

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of increasing muscle growth, performance, resistance to injury and/or preventing or reducing muscle atrophy in an animal in need thereof, comprising administering a musclin peptide consisting of 33 amino acids and consisting of at least 80% identity to SEQ ID NO:2 to the animal.

2. The method of claim 1, wherein the musclin peptide consists of SEQ ID NO:2.

3. The method of claim 1, wherein the musclin peptide is administered subcutaneously, intramuscularly, subfascia, intravenously, intra-fat, peritoneal, inhaled, by infusion pump, transdermally, intradermally, orally, or rectally.

4. The method of claim 1, wherein the musclin peptide is administered subcutaneously.

5. The method of claim 1, wherein the musclin peptide is administered prior to a medical procedure or stress-inducing event.

6. The method of claim 1, wherein the musclin peptide is administered after a medical procedure or stress-inducing event.

7. The method of claim 1, wherein the musclin peptide is administered after the animal has fasted for more than 6 hours.

8. The method of claim 1, wherein the musclin peptide is administered about an hour before or an hour after ingesting food.

9. The method of claim 1, wherein the animal is a mammal.

10. The method of claim 1, wherein the mammal is a human, dog, cat, or horse.

11. The method of claim 1, wherein the animal has a broken bone.

12. The method of claim 1, wherein the animal has muscle injury.

13. The method of claim 1, wherein the animal has spinal cord or nerve injuries.

14. The method of claim 1, wherein the animal is in forced inactivity after a medical procedure.

15. A method of promoting overall exercise tolerance, physical performance and/or cardiovascular function and/or fitness in an animal in need thereof, comprising administering a musclin peptide consisting of 33 amino acids and consisting of at least 80% identity to SEQ ID NO:2 to the animal.

16. The method of claim 15, wherein the musclin peptide consists of SEQ ID NO:2.

17. A method of increasing biogenesis of mitochondria and adaptation of muscle in an animal in need thereof, comprising administering a musclin peptide consisting of 33 amino acids and consisting of at least 80% identity to SEQ ID NO:2 to the animal.

18. The method of claim 17, wherein the musclin peptide consists of SEQ ID NO:2.

* * * * *